United States Patent
Flood

(10) Patent No.: US 8,433,417 B2
(45) Date of Patent: Apr. 30, 2013

(54) CARBON NANOSTRUCTURE ARTIFICIAL RETINAL IMPLANT

(75) Inventor: Dennis J. Flood, Oberlin, OH (US)

(73) Assignee: Newcyte, Inc., Sudbury, MA (US)

( * ) Notice: Subject to any disclaimer, the term of this patent is extended or adjusted under 35 U.S.C. 154(b) by 579 days.

(21) Appl. No.: 12/119,117

(22) Filed: May 12, 2008

(65) Prior Publication Data

US 2008/0288067 A1   Nov. 20, 2008

Related U.S. Application Data

(60) Provisional application No. 60/917,268, filed on May 10, 2007.

(51) Int. Cl.
*A61N 9/08* (2006.01)

(52) U.S. Cl.
USPC .............................. 607/54; 607/53

(58) Field of Classification Search ............ 607/54; 600/383
See application file for complete search history.

(56) References Cited

U.S. PATENT DOCUMENTS

| | | | |
|---|---|---|---|
| 3,150,999 | A | 9/1964 | Rudenberg et al. |
| 5,397,350 | A | 3/1995 | Chow |
| 5,424,054 | A | 6/1995 | Bethune et al. |
| 5,454,880 | A | 10/1995 | Sariciftci et al. |
| 5,747,161 | A | 5/1998 | Iijima et al. |
| 5,895,415 | A * | 4/1999 | Chow et al. ............. 607/54 |
| 5,908,585 | A | 6/1999 | Shibuta et al. |
| 6,207,229 | B1 | 3/2001 | Bawendi et al. |
| 6,559,375 | B1 | 5/2003 | Meissner et al. |
| 6,683,783 | B1 | 1/2004 | Smalley et al. |
| 6,755,530 | B1 * | 6/2004 | Loftus et al. .......... 351/246 |

(Continued)

FOREIGN PATENT DOCUMENTS

| KR | 100649743 B1 | 11/2006 |
|---|---|---|
| WO | WO-03043934 | 5/2003 |

(Continued)

OTHER PUBLICATIONS

Alan Y. Chow, MD; Vincent Y. Schow, BS; Kirk H. Packo, MD; John S. Pollack, MD; Gholan A. Peyman, MD; Ronald Schuchard, PhD The Artifical Silicon Retina Microchip for the Treatment of Vision Loss From Retinitis Pigmentosa , Arch Opthalmol/vol. 122, Apr. 2004 www.archophthalmol.com.

(Continued)

*Primary Examiner* — Carl H Layno
*Assistant Examiner* — Paula J Stice
(74) *Attorney, Agent, or Firm* — Winstead PC

(57) ABSTRACT

A retinal implant can include an array of photoreceptors adapted for positioning in the eye. Each photoreceptor can include a core, for example a carbon nanostructure, and a shell. The shell can include a light-responsive layer, and in many cases, the light-responsive layer can be formed of two semiconductor layers forming a heterojunction. The photoreceptors can be adapted to generate an electric field in response to incident light so as to stimulate a retinal neuron in its vicinity. The photoreceptors can be micron-sized or nano-sized, and can be arranged in densities similar to the density of rods and cones in the human eye. In one embodiment, an exemplary sensor for an imaging device can include a plurality of photosensors disposed on a substrate. Each photosensor can include a carbon nanostructure, a light-responsive layer coating at least a portion of the carbon nanostructure.

25 Claims, 16 Drawing Sheets

U.S. PATENT DOCUMENTS

| | | | |
|---|---|---|---|
| 6,918,946 B2 | 7/2005 | Korgel et al. | |
| 6,946,597 B2 | 9/2005 | Sager et al. | |
| 6,969,897 B2 | 11/2005 | Kim, II | |
| 6,976,998 B2 | 12/2005 | Rizzo et al. | |
| 7,003,354 B2 | 2/2006 | Chow et al. | |
| 7,047,080 B2 | 5/2006 | Palanker et al. | |
| 7,127,301 B1* | 10/2006 | Okandan et al. | 607/116 |
| 7,253,014 B2 | 8/2007 | Barron et al. | |
| 7,494,840 B2* | 2/2009 | Zhang et al. | 438/85 |
| 2002/0076846 A1 | 6/2002 | Ihm | |
| 2002/0084504 A1 | 7/2002 | Narayan | |
| 2004/0023317 A1 | 2/2004 | Motamedi et al. | |
| 2004/0108298 A1 | 6/2004 | Gao | |
| 2005/0089684 A1 | 4/2005 | Barron et al. | |
| 2006/0036045 A1 | 2/2006 | Wilson et al. | |
| 2006/0145194 A1 | 7/2006 | Barron et al. | |
| 2006/0148272 A1 | 7/2006 | Barron | |
| 2006/0186502 A1 | 8/2006 | Shimotani | |
| 2006/0249203 A1 | 11/2006 | Li et al. | |
| 2007/0005116 A1* | 1/2007 | Lo | 607/54 |
| 2007/0111368 A1* | 5/2007 | Zhang et al. | 438/99 |
| 2008/0023067 A1 | 1/2008 | Hu et al. | |
| 2008/0171204 A1 | 7/2008 | Barron et al. | |
| 2010/0249877 A1* | 9/2010 | Naughton | 607/54 |

FOREIGN PATENT DOCUMENTS

| | | |
|---|---|---|
| WO | WO-2004042432 | 5/2004 |
| WO | WO-2004044948 | 5/2004 |
| WO | WO-2004046023 | 6/2004 |
| WO | WO-2005000735 | 6/2005 |
| WO | 2007041293 A2 | 4/2007 |
| WO | WO-2007040594 | 4/2007 |
| WO | WO-2007041293 | 4/2007 |
| WO | 2007084540 A2 | 7/2007 |
| WO | WO-2007084540 | 7/2007 |

OTHER PUBLICATIONS

International Search Report and Written Opinion for PCT. App. No. PCT/US2008/063404, mailed Sep. 12, 2008, 15 Pages.

International Search Report and Written Opinion for PCT App. No. PCT/US08/063076, mailed Sep. 16, 2008, 13 Pages.

Ryan Loscutova and Andrew R. Barron, Coating single-walled carbon nanotubes with cadmium chalcogenides, Loscutova Article, The Royal Society of Chemistry 2005, *J.Mater. Chem.*, 2005, 15, 4346-4353, www.rsc.org/materials.

Translation of KR Published Application No. 10-06497343 (App. No. 10-2005-0099304), As shown on the application it is dated Nov. 27, 2006.

Z. F. Ren et al., "Growth, Characterization, and Potential Applications of Periodic Carbon Nanotube Arrays", 23rd Army Science Conference, Dec. 2-5, 2002, Orlando, Florida.

Junqing Hu, "Tapered Carbon Nanotubes From Activated Carbon Powders," Advanced Materials 2006, 18, 197-200.

"Visible Light Transmitted Through Nanocable," Photonics.com Jan. 8, 2007 (www.photonics.com/Article.aspx?AID=28119).

Jeff Hecht, "Nanoscopic 'Coaxial Cable' Transmits Light," New Scientist Jan. 8, 2007 (www.newscientist.com/article/dn10911-nanoscopic-coaxial-cable-transmits-light.html).

All references listed in the IDS memoranda for U.S. Appl. No. 12/108,500.

* cited by examiner

CARBON NANOSTRUCTURE ARTIFICIAL RETINAL IMPLANT

This application claims the benefit of U.S. Provisional Application No. 60/917,268, titled "Artificial Retina Implant" and filed May 10, 2007, the teachings of which are hereby incorporated by reference.

FIELD

This application generally relates to photosensing devices and methods, and more particularly but not exclusively to photosensing devices and methods for use in the human eye and in imaging devices.

BACKGROUND

Use of semiconductors and other materials that absorb electromagnetic radiation and as a result produce an electrical signal are known. A variety of optical sensors and photo detectors are known. By way of example, the electrical signals from such devices can be used to produce optical images on television and computer monitor screens. Present attempts to make optical sensing devices make use of photolithographic (PL) systems to define devices in two dimensions. Devices are then made in a planar configuration. However, a major problem with such systems, as well as other prior art, is the inability to achieve image resolution comparable to that of the human eye.

Accordingly, there is a need for improved photosensing devices and imaging systems.

SUMMARY

Photosensing devices and methods are disclosed. In one embodiment, an exemplary artificial retinal implant can include a plurality of photoreceptors adapted for positioning in the eye. Each of the photoreceptors can have a core that includes a carbon nano structure (for example, a carbon nanotube, such as a single-wall or multi-wall carbon nanotube) and a shell that includes a light-responsive semiconducting material. The photoreceptors can be adapted to generate an electric field in response to incident light so as to cause an action potential in at least one retinal neuron. In many embodiments, the plurality of photoreceptors can be adapted for implantation on or in the retina. The photoreceptors can have tubular structures with widths in a range of about 1 nm to about 10,000 nm. The photoreceptors can be coupled to a substrate, and can be arranged in a two-dimensional array over a surface of the substrate. The photoreceptors can exhibit a surface density on the substrate in a range of about $10^3/\text{mm}^2$ to about $10^9/\text{mm}^2$. In other embodiments, the photoreceptors can exhibit a density in a range of about 1,000 to about 1,000,000 per square millimeter, about 10,000 to about 1,000,000 per square millimeter, about 100,000 to 1,000,000 per square millimeter, about 500,000 to about 1,000,000 per square millimeter, or about $10^6$ to about $10^9$ per square millimeter.

In another embodiment, an exemplary implantable photoreceptor can include a carbon nanostructure (for example, a carbon nanotube) and a light-responsive layer coating at least a portion of a surface of the carbon nanostructure. The light-responsive layer can generate, in response to light incident thereon, an electric field external to the photoreceptor suitable to induce an action potential in a neuron (for example, by producing an electric charge in the carbon nanostructure, the light responsive layer, or elsewhere in response to incident light). In some embodiments, the electric field generated by the light-responsive layer can have a strength in a range of about 1000 Volts/$\text{cm}^2$ to about 100,000 Volts/$\text{cm}^2$.

The light-responsive layer of the photoreceptor can further include a first layer disposed on the carbon nanostructure and a second layer disposed on the first layer to form a junction therewith. The junction can include a depletion region. At least one of the first and second layers can be made of or include a semiconductor material, which can be of differing conductivity types for each layer. For example, at least one of the first and second layers can include a Group IV semiconductor, a Group III-V semiconductor, a Group II-VI semiconductor, and a Group I-III-VI semiconductor.

Further, the light-responsive layer can coat at least a portion (e.g., an end portion) of the surface of the nanostructure such that a coated end of the nanostructure has a radius of curvature of less than about $10^{-6}$ cm. In other embodiments, the carbon nanostructure can have a tapered end to enhance an electric field produced therefrom. In some embodiments, a wavelength-selective layer can be disposed over the light-responsive layer.

The photoreceptor can also include a substrate supporting the carbon nanostructure. The substrate can comprise a disk, can be annular, or can have other shapes. More than one carbon nanostructure can be provided with the plurality of carbon nanostructures to form a bundle of carbon nanostructures. The light-responsive layer can coat at least a portion of the bundle of carbon nanostructures. The bundle can have a tapered end so as to enhance an electric field produced therefrom. In some embodiments, the light-responsive layer can coat at least a portion of each carbon nanostructure in the bundle of the carbon nanostructures.

The photoreceptor can also include an insulating layer disposed on top of the light-responsive layer. In such an embodiment, the light-responsive layer can be effective to generate, in response to light incident thereon, an electric charge in a portion of the photoreceptor. The electric charge can produce an electric field external to the photoreceptor suitable to induce an action potential in at least one neuron adjacent the insulating layer. In other embodiments, regardless of whether the implant has an insulating layer, the light-responsive layer is operable to generate an electric charge in a portion of the photoreceptor, the electric charge producing an electric field external to the photoreceptor suitable to induce an action potential in at least a neuron located at least about 10 nm, or in some cases at least about 50 nm, from the implantable photoreceptor. In some embodiments, the insulating layer can be disposed on at least a portion of the surface of the carbon nanostructure that is not coated with the light-responsive layer.

The dimensions of the photoreceptor can vary widely. In one embodiment, the carbon nanostructure can have a length of about 2 to 50 microns and a width of about 500 to 2000 nm. The light-responsive layer can have a thickness of about 250 to 2000 nm.

In another embodiment, an exemplary retinal implant includes a plurality of photoreceptors disposed on a substrate (for example, a disk-shaped, annular, or substrate of another shape). At least one of the photoreceptors includes a carbon nanostructure and a light-responsive layer coating at least a portion of a surface of the carbon nanostructure. The light-responsive layer can generate, in response to light incident thereon, an electric field external to the photoreceptor suitable to induce an action potential in a neuron. The plurality of photoreceptors can be disposed on the substrate with a density in a range of about $10^3$ to about $10^9$ photoreceptors per square millimeter, and in some embodiments about 1,000 to about 1,000,000 photoreceptors per square millimeter. Further, the at least one photoreceptor can include a plurality of carbon nanostructures forming a bundle of carbon nanostructures and the light-responsive layer can coat at least a portion of the bundle of carbon nanostructures.

In yet another aspect, an exemplary implantable photoreceptor is disclosed, which can include a carbon nanostructure (for example, a carbon nanotube) and a light-responsive layer coating at least a portion of a surface of the carbon nanostructure. The light-responsive layer can generate, in response to light incident thereon, a current suitable to induce an action potential in a neuron electrically coupled to the photoreceptor. For example, the light-responsive layer can generate, in response to light incident thereon, a current suitable to induce an action potential in a neuron electrically coupled to the photoreceptor and located at least about 1 nm from the implantable photoreceptor.

The photoreceptor can further include an electrical coupling for carrying current between the carbon nanostructure and a neuron, the electrical coupling extending away from the portion of the carbon nanostructure coated with the light-responsive layer. For example, the electrical coupling can include a portion of the carbon nanostructure other than the portion coated with the light-responsive layer. By way of example, the electrical coupling can include a stem cell, or the electrical coupling can include a nanowire.

The photoreceptor can further include an insulating layer disposed on at least a portion of a surface of the carbon nanostructure other than the portion coated with the light-responsive layer and extending towards a neuron to carry current thereto. In other embodiments, the photoreceptor can also include an insulating layer disposed on top of the light-responsive layer. In some embodiments, a wavelength-selective layer can be disposed over the light-responsive layer.

The light-responsive layer of the photoreceptor can further include a first layer disposed on the carbon nanostructure and a second layer disposed on the first layer to form a junction therewith. The junction can include a depletion region. At least one of the first and second layers can be made of or include a semiconductor material, which can be of differing conductivity types. For example, at least one of the first and second layers can include a Group IV semiconductor, a Group III-V semiconductor, a Group II-VI semiconductor, and/or a Group I-III-VI semiconductor.

The photoreceptor can also include a substrate supporting the carbon nanostructure. The substrate can comprise a disk, can be annular, or can have other shapes. More than one carbon nanostructure can be provided, the plurality of carbon nanostructures forming a bundle of carbon nanostructures with the light-responsive layer coating at least a portion of the bundle of carbon nanostructures. The bundle can have a tapered end. In some embodiments, the light-responsive layer can coat at least a portion of each carbon nanostructure in the bundle of carbon nanostructures.

The dimensions of the photoreceptor can vary widely. In one embodiment, the carbon nanostructure can have a length of about 2 to about 50 microns and a width of about 500 to about 2000 nm. The light-responsive layer can have a thickness of about 250 to about 2000 nm.

In another embodiment, an exemplary retinal implant includes a plurality of photoreceptors disposed on a substrate (for example, a disk-shaped, annular, or substrate of another shape). At least one of the photoreceptors includes a carbon nanostructure and a light-responsive layer coating at least a portion of a surface of the carbon nanostructure. The light-responsive layer can generate, in response to light incident thereon, a current suitable to induce an action potential in a neuron coupled to the photoreceptor via the electrical coupling. The plurality of photoreceptors can be disposed on the substrate with a density in a range of about $10^3$ to about $10^9$ photoreceptors per square millimeter, and in some embodiments in a range of about 1,000 to about 1,000,000 photoreceptors per square millimeter. Further, in some embodiments, the at least one photoreceptor can include a plurality of carbon nanostructures forming a bundle of carbon nanostructures. The light-responsive layer can coat at least a portion of the bundle of carbon nanostructures.

Photosensing methods are also disclosed. In one embodiment, a method for stimulating a neuron in the eye can include generating, in response to light, electron-hole pairs in a light-responsive layer that includes a junction with a depletion region, separating the electron-hole pairs across the junction to accumulate electric charge, transporting the electric charge towards a neuron via a carbon nanostructure, and inducing an action potential in a neuron (e.g., a neuron located in a patient's retina) with an electric field produced by the electric charge. In some embodiments, the method can further include enhancing the electric field produced by the electric charge using a tapered surface. The method can also include filtering the light through a wavelength-selective layer so that generation of electron-hole pairs occurs only in response to light of selected wavelengths.

In another embodiment, a method for stimulating a neuron in an eye can include providing a plurality of photoreceptors, each having a carbon core and a light-responsive shell and implanting the photoreceptors in an eye such that the photoreceptors induce an action potential in one or more retinal neurons in response to light incident thereon. The shell can include a first layer disposed on the carbon nanostructure and a second layer disposed on the first layer to form a junction therewith, the junction including a depletion region. The light-responsive layer can generate, in response to light incident thereon, an electric field external to the photoreceptor suitable to induce an action potential in a neuron and/or a current suitable to induce an action potential in a neuron electrically coupled to the photoreceptor. The photoreceptors can be disposed on a disk-shaped substrate, an annular substrate, or a substrate of another shape.

In another embodiment, a method for stimulating a neuron in an eye can include illuminating a plurality of artificial photoreceptors disposed in an eye; generating at least one of an electric field and an electric current in one or more of the artificial photoreceptors in response to the illumination; and inducing an action potential in one or more neurons in proximity to the one or more artificial photoreceptors with the generated electric field or electric current. The plurality of photoreceptors can be arranged on a substrate with a density of about $10^3$ to about $10^9$ photoreceptors per square millimeter, and in some embodiments in a range of about 1,000 to about 1,000,000 photoreceptors per square millimeter. In some embodiments, each photoreceptor comprises a carbon core and a shell comprising a light-responsive layer. The carbon core can include one or more carbon nanotubes. Further, the carbon core can have a length of about 2 to about 50 microns and a width of about 500 to about 2000 nm, and the light-responsive layer can have a thickness of about 250 to about 2000 nm.

Sensors for imaging devices are also disclosed. In one embodiment, an exemplary sensor for an imaging device includes a plurality of photosensors disposed on a substrate. One or more of the photosensors can include a carbon nanostructure, a light-responsive layer coating at least a portion of the carbon nanostructure, a first contact disposed on the substrate and electrically coupled to at least one of the carbon nanostructures, and a second contact disposed on the substrate and electrically coupled to the light-responsive layer. At least one of a voltage and a current across the first and second contacts can represent a value of a pixel in an image captured by the plurality of photosensors.

A wide array of variations are possible. For example, in some embodiments, the light-responsive layer can include a first layer disposed on the carbon nanostructure and a second layer disposed on the first layer to form a junction therewith, the junction including a depletion region. In other embodiments, the plurality of photosensors are arranged in a ordered array. In yet other embodiments, the sensor can further include a wavelength selective conducting layer disposed on the light-responsive layer of one or more photosensors.

BRIEF DESCRIPTION OF THE DRAWINGS

The devices and methods discussed herein will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. The devices and methods specifically described herein and illustrated in the accompanying drawings are non-limiting exemplary embodiments, as the scope of the present application is defined solely by the claims. Throughout this application, the term "e.g." will be used as an abbreviation of the non-limiting phrase "for example."

A variety of embodiments will be presented herein. It should be understood that the features illustrated or described in connection with one exemplary embodiment may be combined with the features of other embodiments. Such modifications and variations are intended to be included within the scope of the present disclosure.

Generally, the devices and method disclosed herein can provide improved photosensing and imaging devices and methods. In many cases they can offer high resolution and compact size. The devices and methods disclosed herein have a wide range of applications, such as electronic imaging systems (e.g., cameras, scanners, artificial vision), but have particular utility as artificial retinal implants. It should be understood that while many embodiments are described below in the context of retinal implants and stimulating neurons in the human eye, the devices and method disclosed herein are not so limited and can be used in virtually any application (currently-known or later-developed) involving the conversion of light into electricity, electrical signals, and/or neural information. Further, it should be understood that the terms "light" and "radiation" are used interchangeably herein to refer to both visible and invisible radiation.

Figure 1A:
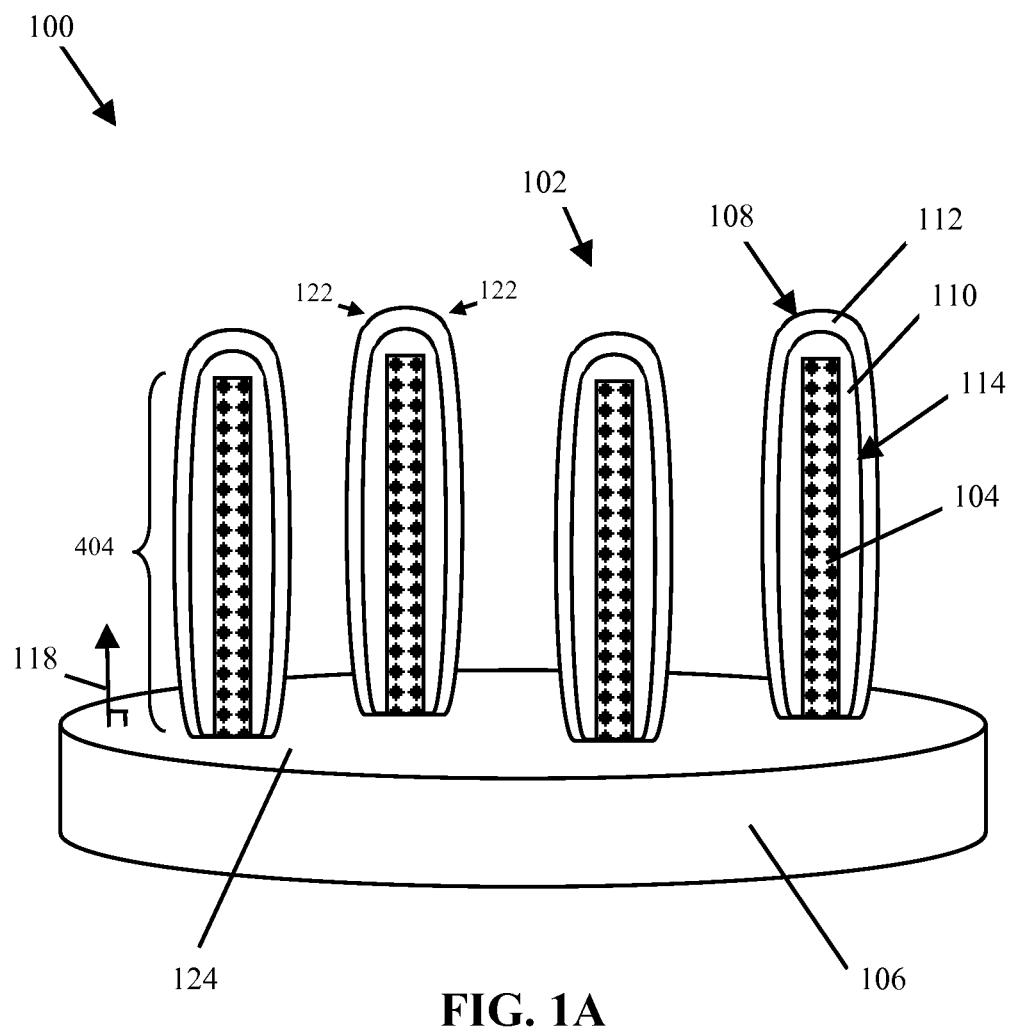
FIG. 1A is a schematic view of one embodiment of a retinal implant which includes a plurality of photoreceptors disposed on a substrate, each photoreceptor having a core covered with a light-responsive layer.
Figure 2:
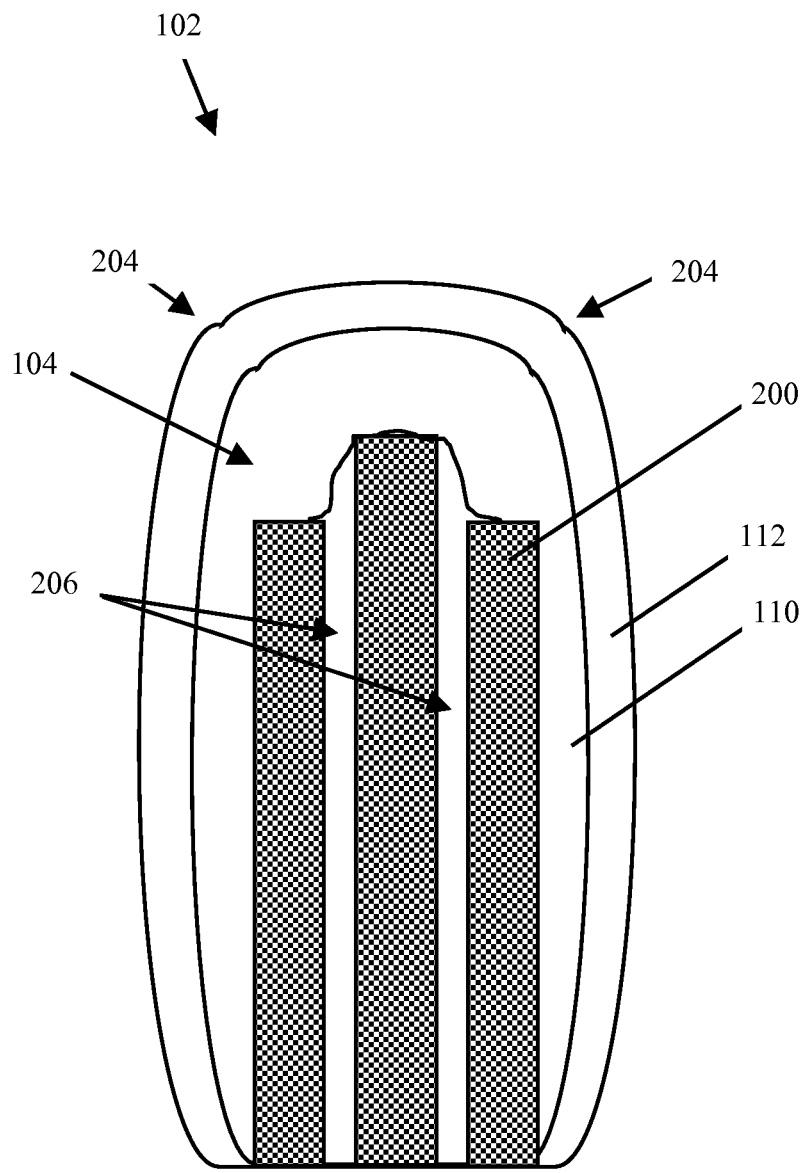
FIG. 2 is a schematic view of one embodiment of a photoreceptor which includes a core formed of individual carbon nanotubes grouped into a bundle and having a light-responsive layer disposed on the bundle.

FIG. 1A schematically illustrates one embodiment of an exemplary artificial retinal implant 100. As shown, the implant 100 includes a plurality of synthetic photoreceptors 102 supported by a substrate 106, each of which has a core 104. In some embodiments, the core 104 is an elongate structure and can be a microstructure or nanostructure, such as a carbon nanotube (e.g., a single wall carbon nanotube (SWNT) or a multiwall carbon nanotube (MWNT)). In some embodiments, individual carbon nanotubes can be used as a core 104, but in the illustrated embodiment of FIG. 1A, core 104 represents a plurality of nanotubes that are grouped into a bundle. FIG. 2 shows the core 104 as a bundle of individual nanotubes 200. Any number or arrangement of carbon nanotubes can be used in such a bundle. For example, the bundles can have a cross-sectional shape that is circular, square, rectangular, oval, or virtually any other shape.

Other carbon nanostructures, including cylindrical, spherical, elongate, ovoid, oblate, and other shapes, can also be used. Buckyballs and structures formed from $C_{60}$ molecules, $C_{72}$ molecules, $C_{84}$ molecules, $C_{96}$ molecules, $C_{108}$ molecules, or $C_{120}$ molecules can also be used. In many embodiments, carbon nanostructures are formed primarily of carbon atoms (e.g., carbon can constitute 90% or more of a nanostructure's composition). However, they can include other constituents, for example, a plurality of catalyzing iron atoms from carbon nanostructure fabrication.

As shown in FIG. 1A, the core 104 of a photoreceptor 102 can be surrounded by a shell, which in this embodiment is a coating formed by a light-responsive layer 108. In many cases, a light-responsive layer 108 is a layer that generates or effects generation of an electric potential in response to incident light of particular wavelengths. In some embodiments, in which photoreceptors 102 are incorporated into retinal implants, the electric potential generated by the light-responsive layer 108 can in turn facilitate generation of an action potential in one or more neuronal cells. In other embodiments, in which photoreceptors 102 are incorporated into image sensors (as will be discussed in more detail, for example, with respect to FIG. 14), the electrical potential generated by the light-responsive layer 108 can in turn facilitate a detectable electrical signal used as a pixel value in a sensed image.

In many embodiments, the light-responsive layer 108 can be composed of two layers 110, 112 of semiconductors having differing conductivity types. As is known in the art, the conductivity type of a material refers to the type of charge carrier (e.g., electron or hole) that is predominantly responsible for electrical conduction in the material. The junction between two materials formed of different conductivity types can be characterized by a depletion region that supports an electric field, while the junction between two materials formed of similar conductivity types lacks such a depletion region. By way of example, the first layer 110 can be made of n-type Si while the second layer 112 can be made of p-type Si, thus forming a p-n junction 114. As is well known in the art, a p-n junction can have certain characteristics, including the aforementioned depletion region which supports an electric field and built-in voltage, all of which follow from the chosen semiconductor materials and doping profiles, among other things. In some embodiments, the junction 114 can be a p-i-n junction that is formed by the junction of a p-type material, an intrinsic layer (e.g., an undoped or lightly doped semiconductor material), and an n-type material.

As one skilled in the art will understand, virtually any biocompatible material capable of forming a junction with a depletion region can be used in the first and second layers 110, 112 of the light-responsive layer 108. For example, a variety of semiconductors (e.g., Group II-VI, Group IV, or Group III-V elements in binary, ternary, or quaternary forms) and dopants can be used. Examples of such materials include, without limitation, silicon, amorphous silicon, ZnSe, and CuSe. Further, other light-responsive materials of biological nature (e.g., rhodopsin) or non-biological nature (e.g., polymers) can also be used. In some embodiments, the light-responsive layer 108 can include a material that may not be biocompatible (e.g., CdSe, CdTe) so long as the artificial retinal implant includes a biocompatible cover or cap (e.g., a light-transmissive dielectric layer, discussed below in more detail) to isolate the material from the external environment.

Other types of junctions can also be used. For example, the light-responsive layer 108 can be configured as a Schottky diode. In one embodiment, the light-responsive layer 108 can be formed from a semiconductor layer (e.g., Si layer) with a metal film (e.g., a gold film) disposed thereon.

Furthermore, in yet other embodiments, the light-responsive layer 108 does not have a junction. For example, the light-responsive layer 108 can be made at least in part of rhodopsin. As in known, upon absorbing light, rhodopsin can undergo a conformational change which can cause polarization and an electrical potential (for example, as occurs in natural photoreceptor cells containing rhodopsin). Such a rhodopsin-containing light-responsive layer 108 can develop an action potential which can be used to stimulate neuronal cells. As previously mentioned, light-responsive polymers also can be used in the light-responsive layer 108.

In some embodiments, the light-responsive layer 108 can conformally coat the surface of the core 104. Such a conformal coating can take the shape of the contours and/or underlying three-dimensional profile of the core 104, and in some cases can cover surfaces of the cores 104 in many or substantially all directions, e.g., in the nature of a circumferential coating. In some cases, the light-responsive layer 108 can coat at least about 90 percent of the surface of the core 104, but in other embodiments, a smaller proportion of the surface can be coated, e.g., less than about 75 percent, 50 percent, or 25 percent, or 10 percent.

Figure 3:
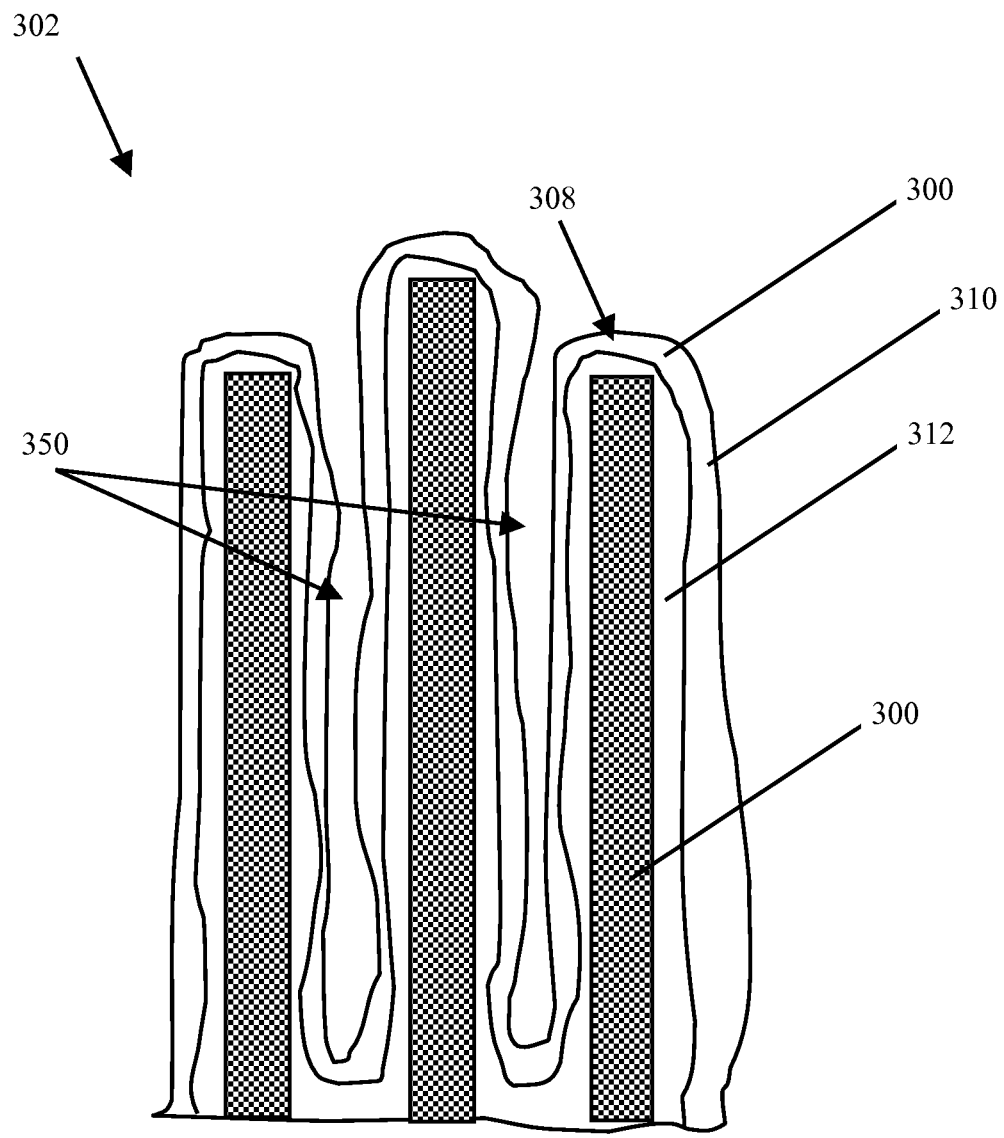
FIG. 3 is a schematic view of one embodiment of a photoreceptor which includes a core formed of individual carbon nanotubes grouped into a bundle and having a light-responsive layer coating individual nanotubes within the bundle.

In embodiments in which the core 104 includes, or is formed of, a bundle of nanotubes, the light-responsive layer 108 can coat the outer surface of the bundle, as is shown in FIG. 2, in which individual nanotubes 200 form a bundle and the layer 110 does not fully extend into the interstices 206 between the nanotubes 200. Alternatively, as is shown in FIG. 3, the light-responsive layer 308 can conformally coat individual nanotubes 300 in a bundle, providing a coating within the interstices 350 between the nanotubes 300. In some embodiments, the coating can at least partially cover at least about 5 percent of the individual nanotubes 300 (or other nanostructures) in the bundle 302; in other embodiments, between 5 and 100 percent of individual nanotubes are at least partially coated. More narrow ranges are possible. For example, the coating can at least partially cover 5 and 10 percent of carbon nanotubes, between 5 and 20 percent, between 5 and 30 percent, about 40 percent, about 50 percent, about 75 percent, and so on. In yet other embodiments, the light-responsive layer 108 can fill up the interstices between individual carbon nanotubes and then be built up to create a planar top surface, which can then be coated, e.g., with a protective and/or insulating layer.

Figure 1B:
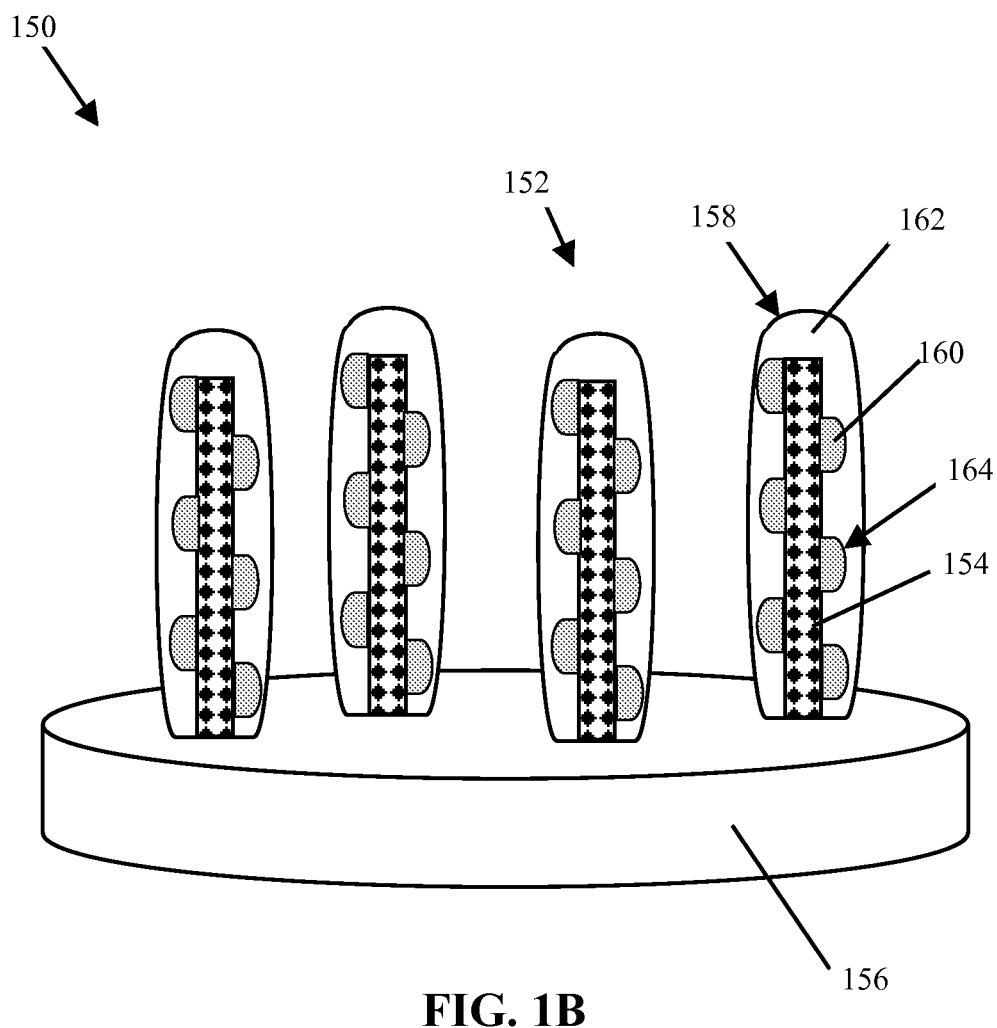
FIG. 1B is a schematic view of another embodiment of a retinal implant which includes plurality of photoreceptors disposed on a substrate, each photoreceptor having a core with a plurality of nanostructures disposed thereon, the core and the plurality of nanostructures being covered with a layer of material.

Although the layers on the bundles and/or nanotubes are shown as films in FIGS. 1A, 2 and 3, in alternate embodiments the layers can be discontinuous, e.g., in the form of individual nanostructures 160 as shown in the exemplary implant 150 of FIG. 1B. For example, the light responsive layer 158 can include a plurality of semiconductor nanostructures 160 (although the nanostructures 160 can be made of another material) disposed on the core 154. The semiconductor nanostructures 160 can be disposed on the surfaces of a bundle forming the core 154, or on the surfaces of individual carbon nanotubes in a bundle. Such semiconductor nanostructures 160 may exhibit quantum effects, e.g., acting as quantum dots, or may be substantially free of quantum confinement effects. A layer 162 (e.g., formed of a semiconductor material) can cover the semiconductor nanostructures 160 and the portions of the core 154 that are not covered with the semiconductor nanostructures 160. The semiconductor nanostructures 160 can be formed from a semiconductor material of the same or differing conductivity type as the layer 162. A junction 164 can be formed at the interface of the nanostructures 160 and layer 162, in effect creating a core 154 with a distributed junction 164. The use of such nanostructures 160 can be advantageous for engineering the band gap of the photoreceptor 152 and tuning its response to desired wavelengths.

Figure 4:
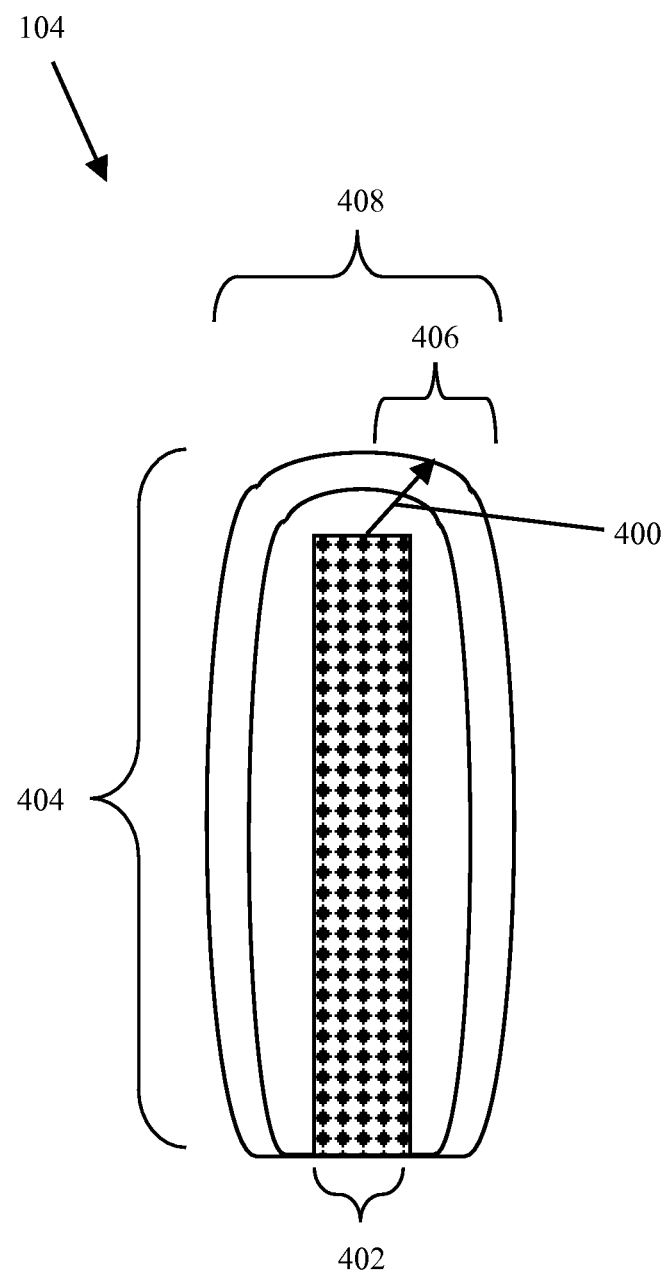
FIG. 4 is a schematic view of a photoreceptor shown in FIG. 1A with exemplary dimensions.

Returning to FIG. 1A, the size of a photoreceptor 102 can vary widely, but in some cases the photoreceptor 102 can be sized to approximately match the size of natural human photoreceptors. In one exemplary embodiment, illustrated in FIG. 4, the core 104 can have a diameter or width 402 in a range of about 500 nm to about 2000 nm and can have a length 404 in a range of about 2000 nm to about 50,000 nm. The light-responsive layer 108 can have a thickness 406 of about 250 nm to about 2000 nm. The overall diameter 408 of the photoreceptor 102, including the core 104 and light-responsive layer 108, can be in a range about 1 micron to about 10 microns. However, all such dimensions can vary widely, for example, in other embodiments the photoreceptors 102 can have overall diameters anywhere from about 1 nm to about 10 microns. It should be understood that all such dimensions are merely illustrative in nature.

As shown in FIG. 1A, the photoreceptors 102 can be disposed on a substrate 106. In this embodiment, the photoreceptors 102 are arranged to stand aligned and disposed in a substantially vertical orientation on the substrate 106. As used herein, a substantially vertical orientation means that the photoreceptors 102 are normal to the substrate 106 or are nearly, but not exactly, normal to the substrate 106. In many embodiments, the photoreceptors 102 can be substantially vertically oriented such that the angle between the photoreceptor 102 (e.g., taken along its length 116) and a vector 118 that is normal to the substrate surface 124 is less than about 45 degrees. It should be understood, however, that the photoreceptors 102 need not be oriented in any particular direction.

Figure 5:
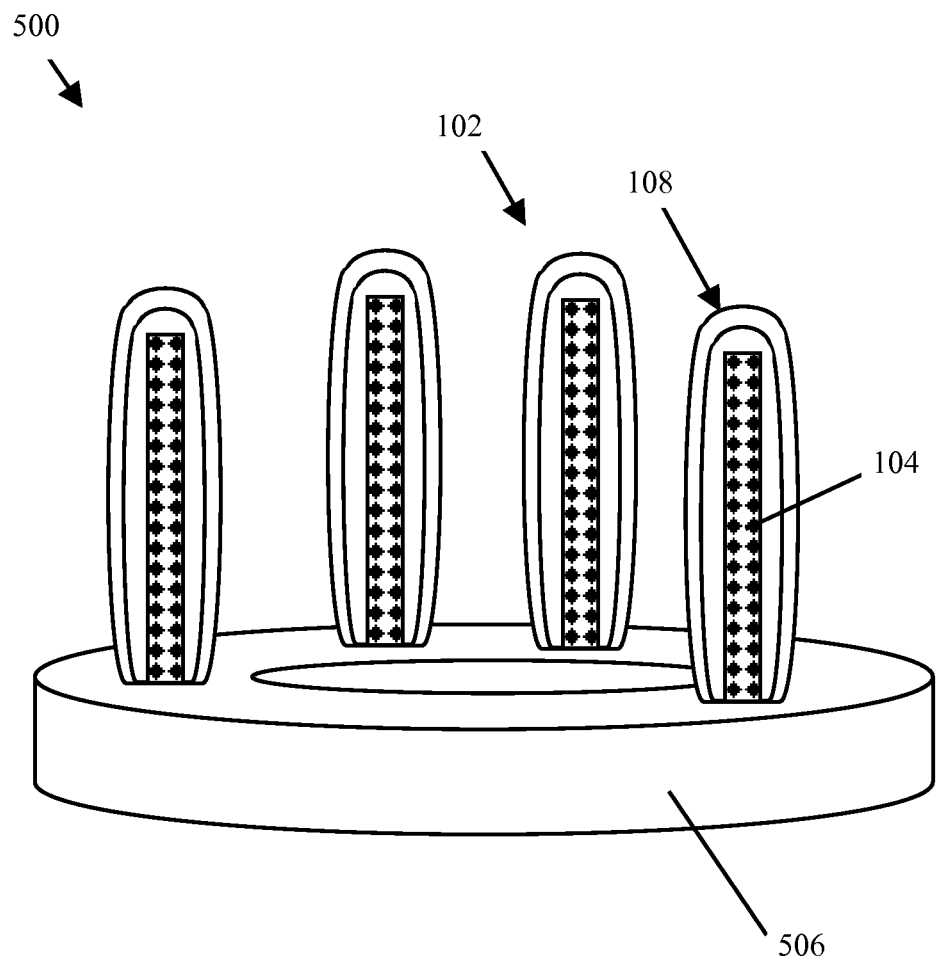
FIG. 5 is a schematic view of another embodiment of a retinal implant which includes a plurality of photoreceptors disposed on an annular substrate, each photoreceptor having a core covered with a light-responsive layer.

The substrate 106 can be in the form of a disk or can have virtually any other shape suitable for implantation in the eye. For example, as illustrated in FIG. 5, the substrate 506 can have an annular shape, which can be advantageous to treat some diseases of the eye, as will be explained in more detail below. The substrate can be electrically conductive, but need not be so. The substrate 106 is preferably rugged enough to withstand surgical placement in the eye, and to survive the environmental conditions existing in the region of the eye where the retinal implant 100 is to be placed (e.g., subretinal or supra-retinal). In some embodiments, the substrate can be flexible, which can be useful in implantation procedures (e.g., by allowing the implant to be flexed or folded when inserted, for example, through a cannula). Typically, for implantation in the eye, the substrate can be formed of a bio-compatible material, or in some cases can be sealed inside a biocompatible cover, as previously mentioned. By way of example, the substrate 106 can be formed of a semiconductor (e.g., a silicon wafer), a metal foil (e.g., gold foil), or a carbon nanostructure (e.g., a mesh of carbon nanotubes). The substrate 106 can be or incorporate a magnetic material so as to have magnetic poles, which can be useful in implanting and aligning the implant, as will be discussed below.

The substrate can have a wide variety of sizes. For example, the substrate can have a width or diameter in a range of about 1 mm to about 40 mm when used for a retinal implant, although the substrate can have virtually any size. The substrate can exhibit larger sizes when used in an imaging device (as will be discussed below). In some embodiments, for example in which a retinal implant has a disk-shaped substrate adapted to be implanted in a central region of the retina, the substrate can have a diameter in a range of about 1 mm to about 5 mm. In other embodiments, for example in which the retinal implant has annular substrate adapted to be implanted in a peripheral region of the retina (e.g., as shown in FIG. 5), the substrate can have a diameter of about 20 mm to about 30 mm. In some embodiments, the substrate can be about 10 to about 1000 microns, and in other embodiments about 50 to about 200 microns thick. All such dimensions, however, are merely illustrative in nature.

A specific number or density of photoreceptors 102 (e.g., on the substrate 106) is not necessary. However, in some embodiments, the density of the photoreceptors 102 is nearly equal to or greater than the density of photoreceptors in the region of the retina in which the retinal implant 100 would be placed. For example, the density of cones in the fovea has been reported to be approximately 180,000 per square millimeter, and the density of rods in the region away from the fovea has been reported to vary from about 40,000 to 160,000 per square millimeter. In other embodiments, the density of natural photoreceptors can be about $10^3/mm^2$ to about $10^9/mm^2$. In yet other embodiments, the density of photoreceptors 102 can be in a range of about 1,000 to about 1,000,000 per square millimeter, or in a range of about 10,000 to about 1,000,000 per square millimeter, in a range of about 100,000 to about 1,000,000 per square millimeter, in a range of about 500,000 to about 1,000,000 per square millimeter, or in a range of about $10^6$ to about $10^9$ per square millimeter.

Figure 6:
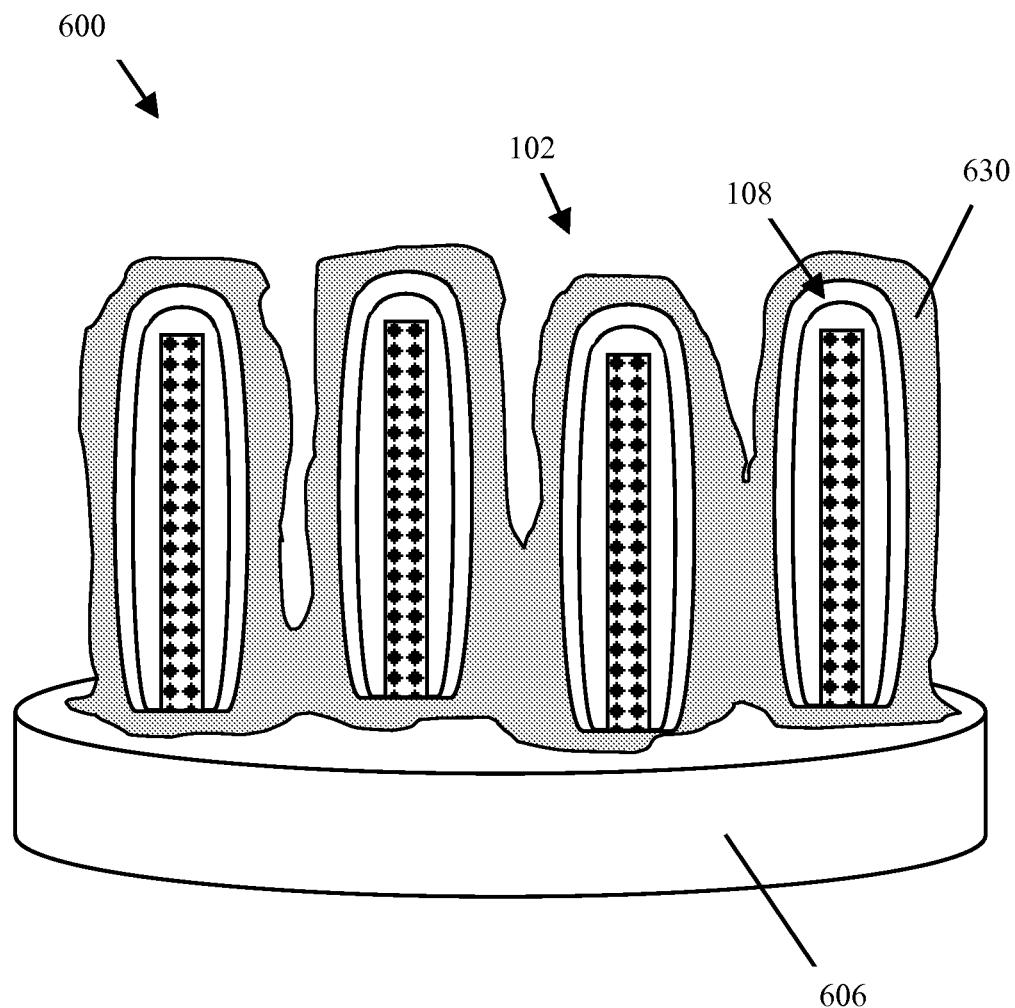
FIG. 6 is a schematic view of the retinal implant shown in FIG. 1A with an insulating layer disposed thereon.

The photoreceptors 102 can be covered (entirely or partially) with an insulating layer 630, as shown in FIG. 6. The insulating layer 630 can be formed of virtually any electrically insulating material, such as silica, ZnO, or other dielectric materials. The insulating layer 630 can also serve as an environmental barrier, for example to isolate the materials used in the photoreceptor from the environment of the eye. Such a barrier can protect the implant 100 from potentially caustic effects of the environment of the eye and can protect the eye from materials used in the artificial retinal implant. The barrier can also serve as a physical support (e.g., by using a rigid or hard layer). In other embodiments, a dedicated environmental barrier (e.g., a silicone or polymeric coating) can be included as an environmental seal in addition to the insulating layer. And additional layers can be included. For example, a wavelength-selective coating (e.g., a coating that filters certain light wavelengths, such as a coating formed of silica layers to which inorganic materials have been added to allow selective light transmission) can be disposed on the photoreceptor 102 (e.g., on top of the light-responsive layer 108) to limit the wavelengths of light to which the photoreceptor 102 is responsive. An anti-reflective coating, such as a silicon oxynitride thin film, can also be provided.

In use, and without being limited by theory, the retinal implant 100 can be placed in the eye and exposed to light that passes through the iris to reach the retina. Some of the photons passing through the second layer 112 of the light-responsive layer 108 can be absorbed (e.g., by the semiconductor material of that layer) to generate electron-hole pairs. Other photons can pass through the second layer 112 to be absorbed by the first layer 110 so as to generate electron-hole pairs therein. The generation of electron-hole pairs occurs, e.g., by promoting an electron in the valence band of the material to its conduction band. As previously mentioned, and for explanatory purposes only, the first layer 110 can be made of n-type semiconductor (e.g., n-type Si), while the second layer 112 can be made of p-type semiconductor (e.g., p-type Si). In such an embodiment, the electric field in the junction 114 causes the separation of such electron-hole pairs in the vicinity thereof. Electrons can travel across the junction 114 to the n-type semiconductor and the holes can travel across the junction 114 to the p-type semiconductor. Additionally, electron-hole pairs are photo-generated outside the vicinity of the depletion region in both the first and second layers 110, 112. Such electrons and holes can move (e.g., diffuse, as dictated by factors such as carrier concentration and thermal effects in the semiconductor) within the first and second layers 110, 112, as the case may be. This movement can be quantitatively described by their diffusion lengths (e.g., average distance traveled by a charge carrier before recombination).

The migration of electrons to the n-type first layer 110 and the holes to the p-type second layer 112 represents an accumulation of electric charge, which can create an electric field extending external to the photoreceptor 102. In many embodiments, the photoreceptor 102 can be adapted to produce an electric field suitable to stimulate one or more neurons in the eye (e.g., bipolar cells or ganglion cells) that is in proximity to the photoreceptor 102. In other words, nerve endings (e.g., nerve endings of bipolar or ganglion cells) that lie within the electric field can be induced to "fire" by developing an action potential as though they are the locus of a synapse. In many embodiments, an electrically conductive physical connection between the photoreceptors 102 of the retinal implant 100 and the nerve endings is not necessary (e.g., the electrical field can be sufficiently strong to cause the cells to "fire" even in the absence of such a direct physical connection). However, in other embodiments an electrically conductive physical connection (e.g., a nanowire) can be provided. The stimulation of a neuron in the retina can cause the neuron to develop an action potential and induce other neurons to fire, beginning a chain of neuronal activity that can transmit a signal through the optic nerve and ultimately to the brain.

In some embodiments, the electric field generated by the photoreceptor or group of photoreceptors can have a strength in range of about 1,000 to about 100,000 Volts/cm in the vicinity of the neuron, and in other embodiments in a range of about 1,000 to about 10,000 Volts/cm. The strength of the electric field can be adapted (e.g. via selection of the dimensions, the thickness and materials used in the photoreceptor 102, and so on) to be suitable for stimulating neurons at a desired distance from the photoreceptor 102. By way of example, the photoreceptors 102 can be adapted to stimulate neurons at a distance anywhere from about 10 nm to about 100 nm. For example, in some embodiments, the photoreceptors 102 can be adapted to stimulate neurons at a distance of at least about 10 nm, and in other embodiments at a distance of at least about 50 nm, or in yet other embodiments at least about 100 nm. All such metrics, however, are merely for illustrative purposes.

As one skilled in the art will understand, in other embodiments the first layer 110 can be made of p-type material, while the second layer 112 can be made of n-type material, and the operation of such a device will mirror that described above, for example electrons can travel across the junction 114 to the n-type semiconductor and the holes can travel across the junction 114 to the p-type semiconductor. Further, the use of heterojunctions are not necessary, as in some embodiments, separation of the charges generated by photon absorption may occur by, without limitation, dissociation of the constituent molecules of some types of absorber layer materials, whereby distinct chemical fragments or even specific ions then transport charge in a manner similar to the way ordinary nerve impulses are propagated.

In some embodiments, an end of the photoreceptors 102 can be tapered. Tapering a photoreceptor 102 can be advantageous for enhancing the electric field produced at the tapered end, which can facilitate the stimulation of retinal cells. The electric field produced outside such a tapered surface at a given electric potential is inversely proportional to its radius of curvature (e.g., exemplary radius of curvature 400 as marked in FIG. 4). In some embodiments, a radius of curvature of about $10^{-6}$ cm or less can be used. In some embodiments, the radius of curvature can be in a range of about $10^{-4}$ cm to $10^{-7}$ cm; however all such dimensions are illustrative in nature and can vary.

Figure 7:
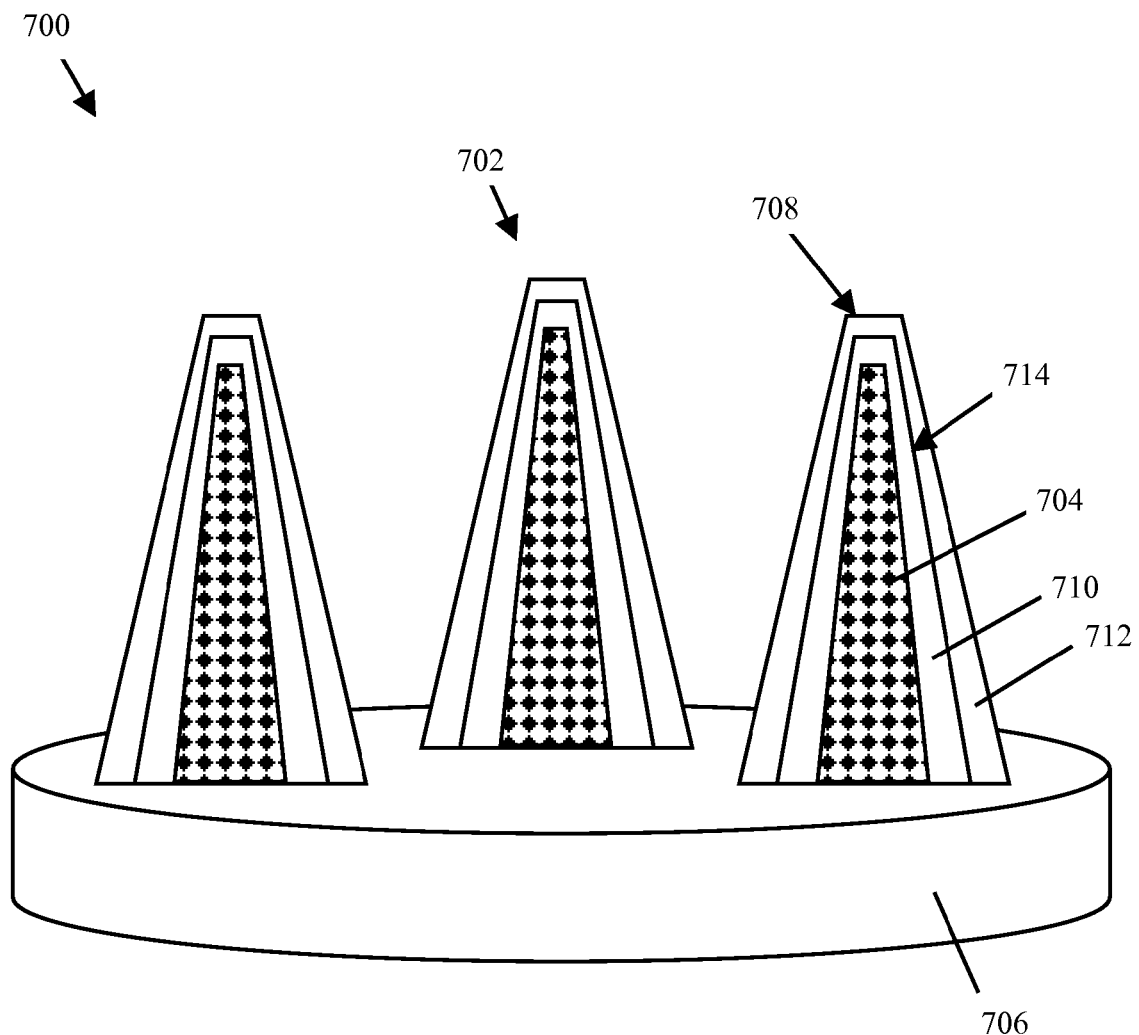
FIG. 7 is a schematic view of another embodiment of a retinal implant which includes a plurality of photoreceptors disposed on a substrate, each photoreceptor having a tapered core and being covered with a light-responsive layer.

Tapering can be accomplished in a variety of ways. For example, in some embodiments the light-responsive layer 108 disposed on the core 104 can form a tapered surface 122, e.g., as a consequence of the deposition process on the surface (e.g., the deposition process being designed to produce a suitable radius of curvature as mentioned above). Further, in embodiments in which the core 104 is formed of a bundle of carbon nanotubes, the carbon nanotubes in the bundle can be arranged (and/or differently sized) so as to exhibit, collectively, a tapered shape, as shown in FIG. 2 by arrows 204. Still further, one or more tapered carbon nanotubes can be used to form the core 104. The growth of tapered nanotubes is known in the art and can be accomplished, for example, via chemical vapor deposition techniques, as described in Hu et al., "Tapered Carbon Nanotubes from Activated Carbon Powders," Advanced Materials, Vol. 18, 197-200 (2006) and U.S. Pat. No. 7,064,474, titled "Carbon Nanotube Array And Field Emission Device Using Same," all of which are hereby incorporated by reference in their entireties. FIG. 7 shows one exemplary embodiment of a retinal implant 700 having photoreceptors 702 with cores 704 which include tapered carbon nanotubes and are coated with a light-responsive layer 708. As shown, the light-responsive layer 708 has two layers 710, 712 forming a junction 714 with a depletion region.

Figure 8:
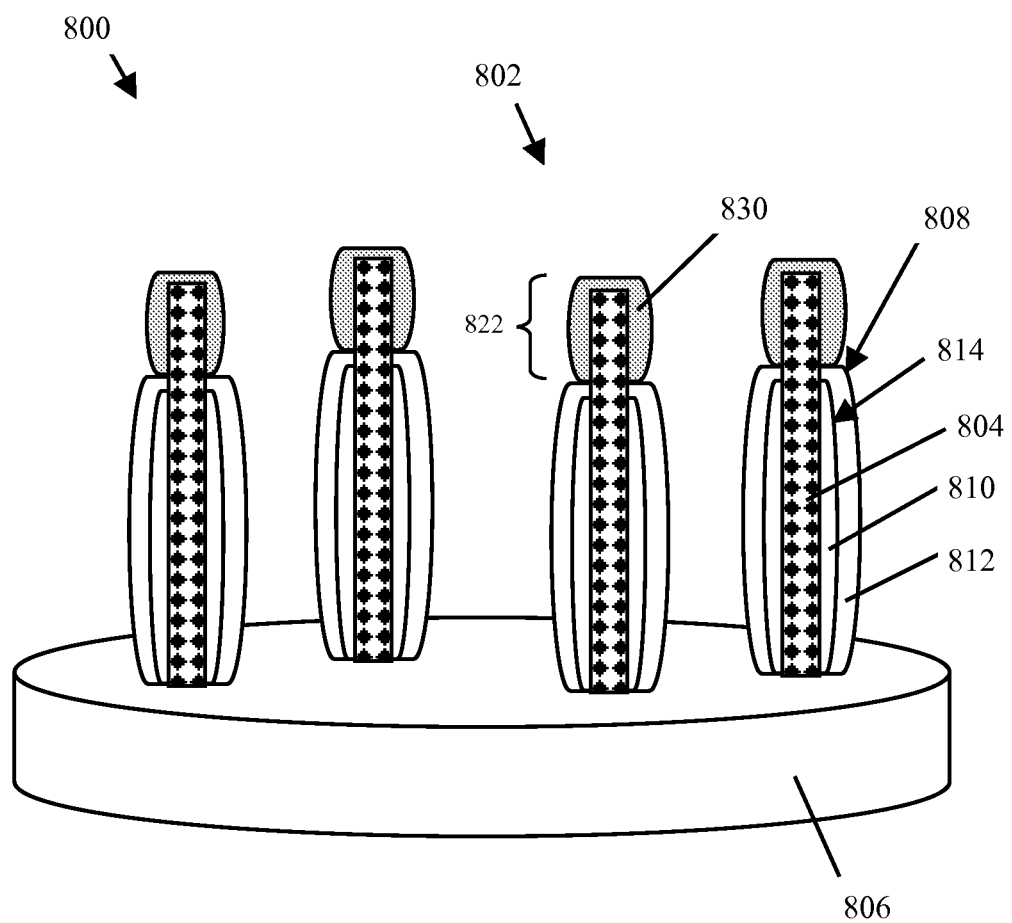
FIG. 8 is a schematic view of another embodiment of a retinal implant which includes a plurality of photoreceptors disposed on a substrate, each photoreceptor having a core, a portion of which is covered with a light-responsive layer and another portion of which is covered with an insulating layer.

FIG. 8 shows yet another exemplary embodiment of a retinal implant 800 which includes a plurality of photoreceptors 802. In this embodiment, each photoreceptor 802 has a core 804 that is partially coated with a light-responsive layer 808, leaving a portion 822 that is not coated with the light-responsive layer 808. That portion 822 of the core 804 can be coated with an insulating layer 830 and can be oriented to extend, for example, towards a neuron when implanted, which can advantageously reduce the separation distance between electric charge accumulated therein and a target neuron, and increase the strength of the electric field on the neuron. Although in the embodiment shown in FIG. 8 the insulating layer 830 coats the entire end of the core 804, in other embodiments, the insulating layer 830 can coat part of the extended portion 822. In operation of such an embodiment, some current may leak from the core 804; however an electric field sufficient to simulate a neuron can still be produced.

Figure 9:
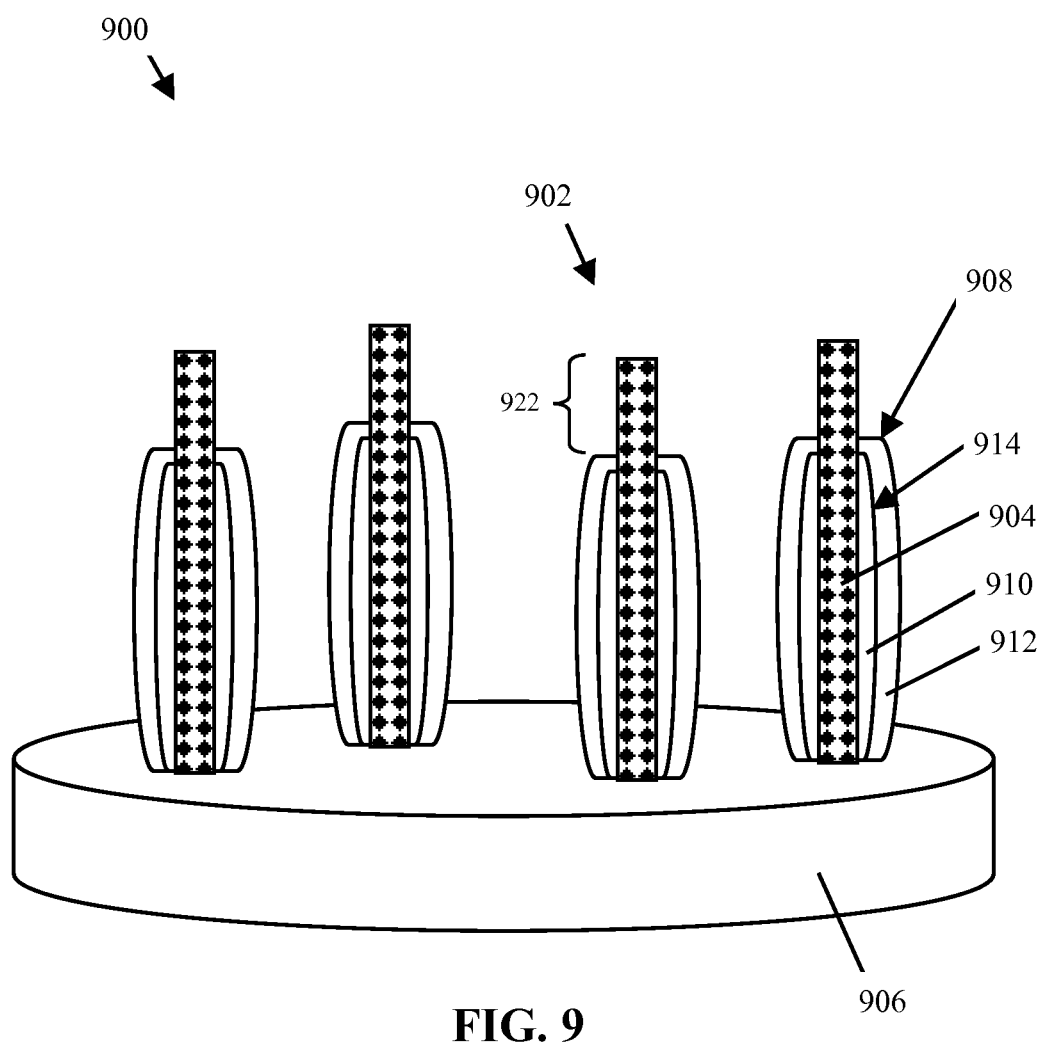
FIG. 9 is a schematic view of another embodiment of a retinal implant which includes a plurality of photoreceptors disposed on a substrate, each photoreceptor having a core, a portion of which is covered with a light-responsive layer and another portion of which is not coated with the light-responsive layer.

In other embodiments, the insulating layer can be omitted from the extended portion, as shown in FIG. 9. FIG. 9 illustrates another exemplary embodiment of a retinal implant 900 which has a plurality of photoreceptors 902 disposed on a substrate 906. Each photoreceptor 902 can have a core 904 covered with a light-responsive layer 908 that includes two layers 910, 912 forming a junction 914, as previously described. An extended portion 922 of the core 904 can remain uncoated.

In use, and without being limited by theory, the artificial retinal implant 900 can be placed in the retina and exposed to light that passes through the iris. Some of the photons passing through the second layer 912 can be absorbed (e.g., by the semiconductor material of that layer) to generate electron-hole pairs. Other incident photons pass through the second layer 912 to be absorbed by the first layer 910 so as to generate electron-hole pairs therein. As previously discussed, and for explanatory purposes only, the first layer 910 can be made of n-type semiconductor (e.g., n-type Si), while the second layer can be made of p-type semiconductor (e.g., p-type Si). In such an embodiment, the electric field in the junction 914 causes the separation of such electron-hole pairs in the vicinity thereof. Electrons can travel across the junction 914 to the n-type semiconductor and the holes can travel across the junction 914 to the p-type semiconductor. Additionally, electron-hole pairs are photo-generated outside the vicinity of the depletion region in both the first and second layers 910, 912. Such electrons and holes can move (e.g., diffuse, as dictated by factors such as carrier concentration and thermal effects in the semiconductor) within the first and second layers 910, 912, as the case may be. Photogenerated electrons can travel to the core 904 (which, as previously mentioned, can be an electrically conductive carbon nanotube) and exit the photoreceptor at portion 922, which is placed in proximity to a neuron. Some electrons may flow to and through the neuron, while other electrons may flow through the retinal tissue and/or vitreous humor filling the eye (e.g., with the retinal tissue and/or vitreous humor presenting an effective resistance) to return to the p-type layer 912 (e.g., to the side of the photoreceptor 902) to recombine with holes that have migrated to that layer 912. The flow of current through and/or in proximity to the neuron can be effective to stimulate it. By way of example, in some embodiments, the current produced can be in a range of about 1 microamp ($10^{-6}$ amps) to about 1 milliamp ($10^{-3}$ amps). The strength of the current can be adapted (e.g., via selection of photoreceptor 102 dimensions, the thickness and materials used in the photoreceptor 902, and so on) to be suitable to stimulate neurons at a desired distance from the photoreceptor 902. By way of example, the current produced can be suitable to induce an action potential in a neuron located in a range of about 1 nm to about 10 nm from the photoreceptor 902. For example, in some embodiments, the current can be suitable to induce an action potential in a neuron at least about 1 nm, and in other embodiments at least about 10 nm from the photoreceptors 902. All such metrics, however, are merely for illustrative purposes.

Figure 10:
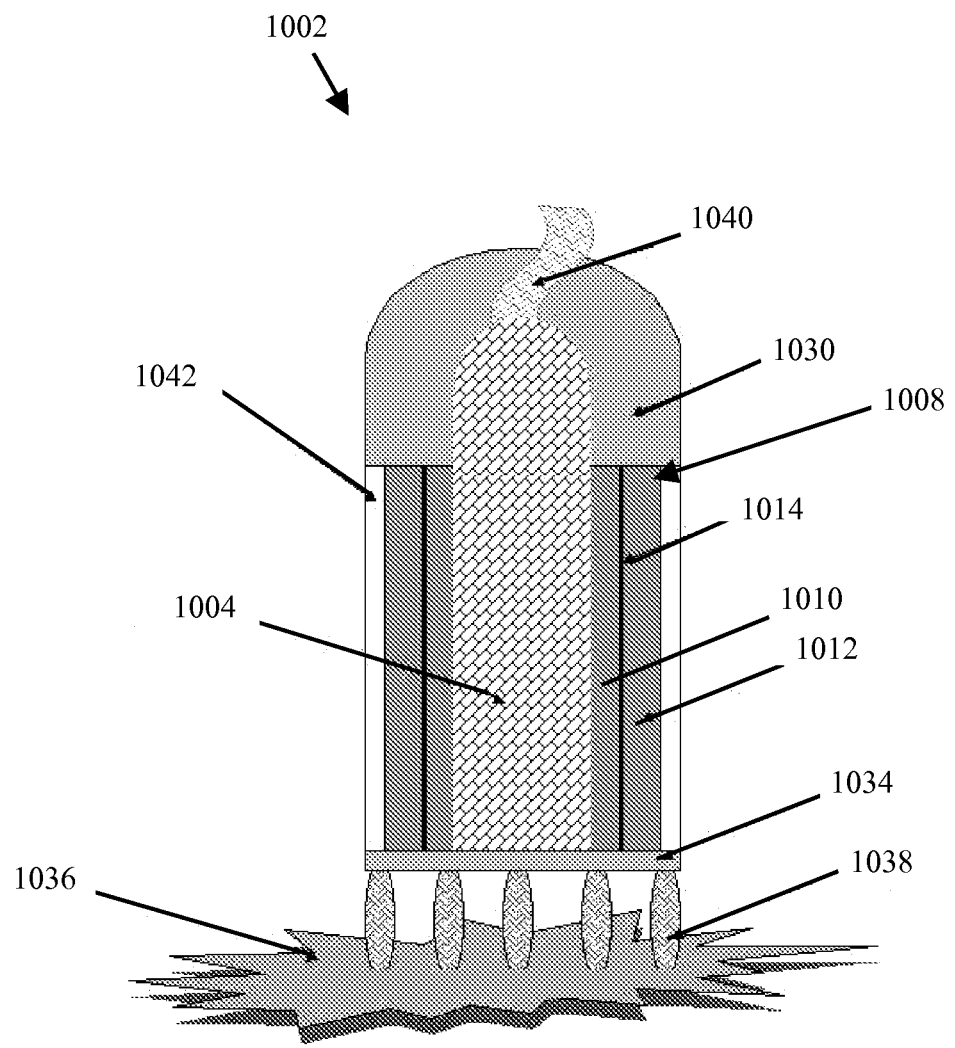
FIG. 10 is a schematic view of another embodiment of a photoreceptor having a core covered with a light-responsive layer, a dielectric layer, and a wavelength-selective layer.

FIG. 10 is a schematic view of another exemplary embodiment of a photoreceptor 1002 which includes a core 1004 (e.g., a carbon nanotube or otherwise) partially covered by a light-responsive layer 1008. The light-responsive layer 1008 can include a first layer 1010 and a second layer 1012 (e.g., semiconductor layers, as previously described) which form a junction 1014. In some embodiments, the interface between the core 104 (which can be a functionalized carbon nanotube) and the light-responsive layer 1008 can have electrical properties such that a charge carrier (e.g., an electron or a negatively charged ion) generated by the absorption of a photon may pass easily from the light-responsive layer 1008 to the core 1004.

A dielectric layer 1030 can be disposed over a portion of the core 1004 (e.g., which is functionalized to accept the dielectric layer 1030). Although in FIG. 10 the dielectric layer 1030 covers a portion of the core 1004 that is not coated with the light-responsive layer 1008, in other embodiments the dielectric layer 1030 can be disposed on top of at least a portion of the light-responsive layer 1008. As previously mentioned, the dielectric layer 1030 can electrically isolate both the core 1004 and the top of the light-responsive layer 108 from the vitreous humor of the eye, or from any other external environment in which the photoreceptor 1002 may be operated.

A coupling 1040 (e.g., an electrically conductive coupling) can be attached to the core 1004 and can extend through the dielectric layer 1030. The coupling 1040 can form an electrical pathway to carry current to or, in the vicinity of, a neuron, as previously described. In some embodiments, the coupling can be formed of a thin filament, which is preferably biocompatible (such as a gold filament). In other embodiments, the coupling 1040 can be formed of a nanowire or a biological component such as a stem cell.

Further, in some embodiments, a wavelength-selective layer 1042 can be disposed on top of the light-responsive layer 1008. The wavelength-selective layer 1042 can be made of a material, such as silica with an additive incorporated therein (e.g., an additive that acts to filter the light, such as iron), that is transparent to light of certain wavelengths but blocks the passage of other wavelengths (or reduces their intensity), thereby adapting the photoreceptor 1002 to respond only to certain selected wavelengths. By way of non-limiting example only, in some cases three different coatings may be used, each with optimal transmission occurring at the following wavelengths, in a manner similar to the absorption by the natural cones in the human eye: 565 nanometers; 540 nanometers; and 435 nanometers. Further, the relative numbers of photoreceptors with the three different coatings can be made to approximate the proportions with such natural photoreceptors are found in the human retina.

The wavelength-selective layer 1042 can be conductive, which can be particularly advantageous in embodiments in which the photoreceptor 1002 is designed to operate by producing a current, as described above in connection with FIG. 9, or can be insulating.

Another dielectric layer 1034 can be disposed on the bottom end of the photoreceptor 1002 (e.g., by functionalizing the end to accept the dielectric material). One or more attachment mechanisms 1038 can be used to anchor the photoreceptor 1002 to the retina 1036. The photoreceptor can be anchored to a variety of locations in the retina, such as the pigment epithelium, the layer of rods and cones, the layer of bipolar cells or ganglion cells, the inner or outer limiting membrane, or in other locations. The nature of the attachment mechanism 1038 can vary, but in some embodiments a bioadhesive (e.g., proteins or gels) can be used. In other embodiments, stem cells or other biological structures or molecules can be used to anchor the photoreceptor. The free end of such biological structures can be functionalized to attach to retinal tissue, such as the pigment epithelium 1036, or to a substrate that is implanted. In some embodiments, the photoreceptor 1002 can be placed in the retinal tissue without anchoring so that it is physically secured by the surrounding tissue.

It should be understood that any of the features (e.g., dimensions, materials, tapering, and so on) described in connection with previously-discussed photoreceptors can be incorporated into photoreceptor 1002. In use, implant 1000 can produce an electric field and/or a current suitable for stimulating a neuron, as previously described.

Figure 11:
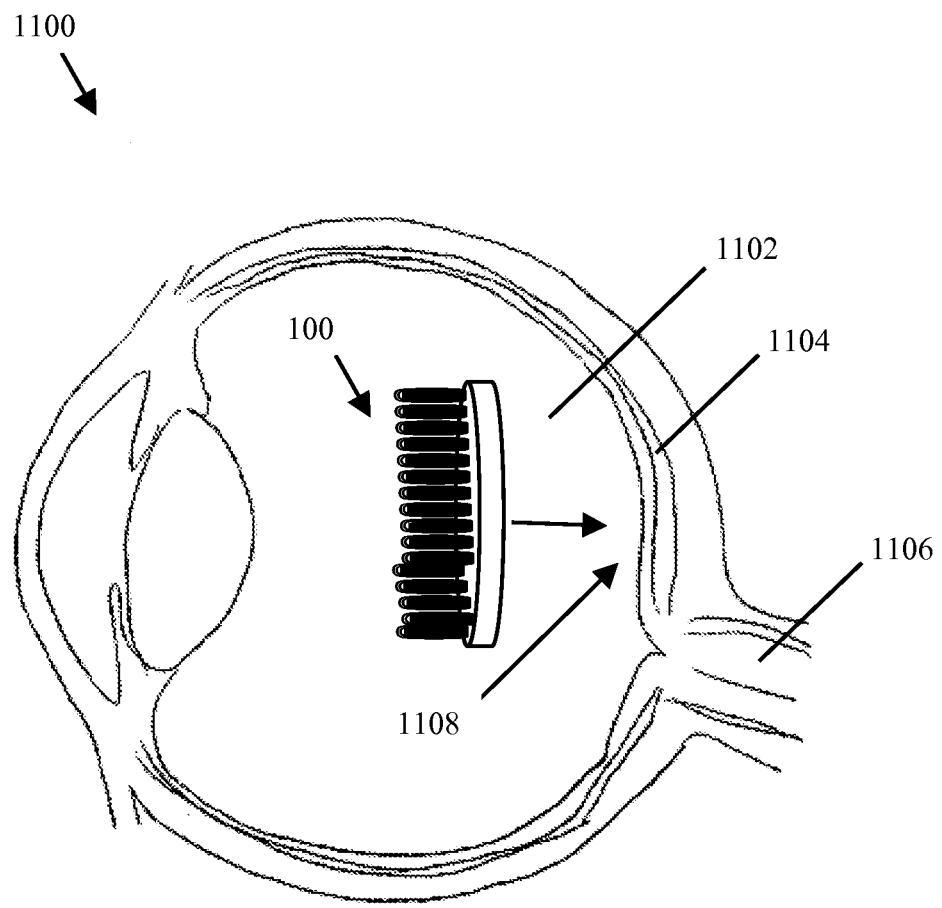
FIG. 11 is a schematic view illustrating one embodiment of a method of implanting a retinal implant in the eye.
Figure 12:
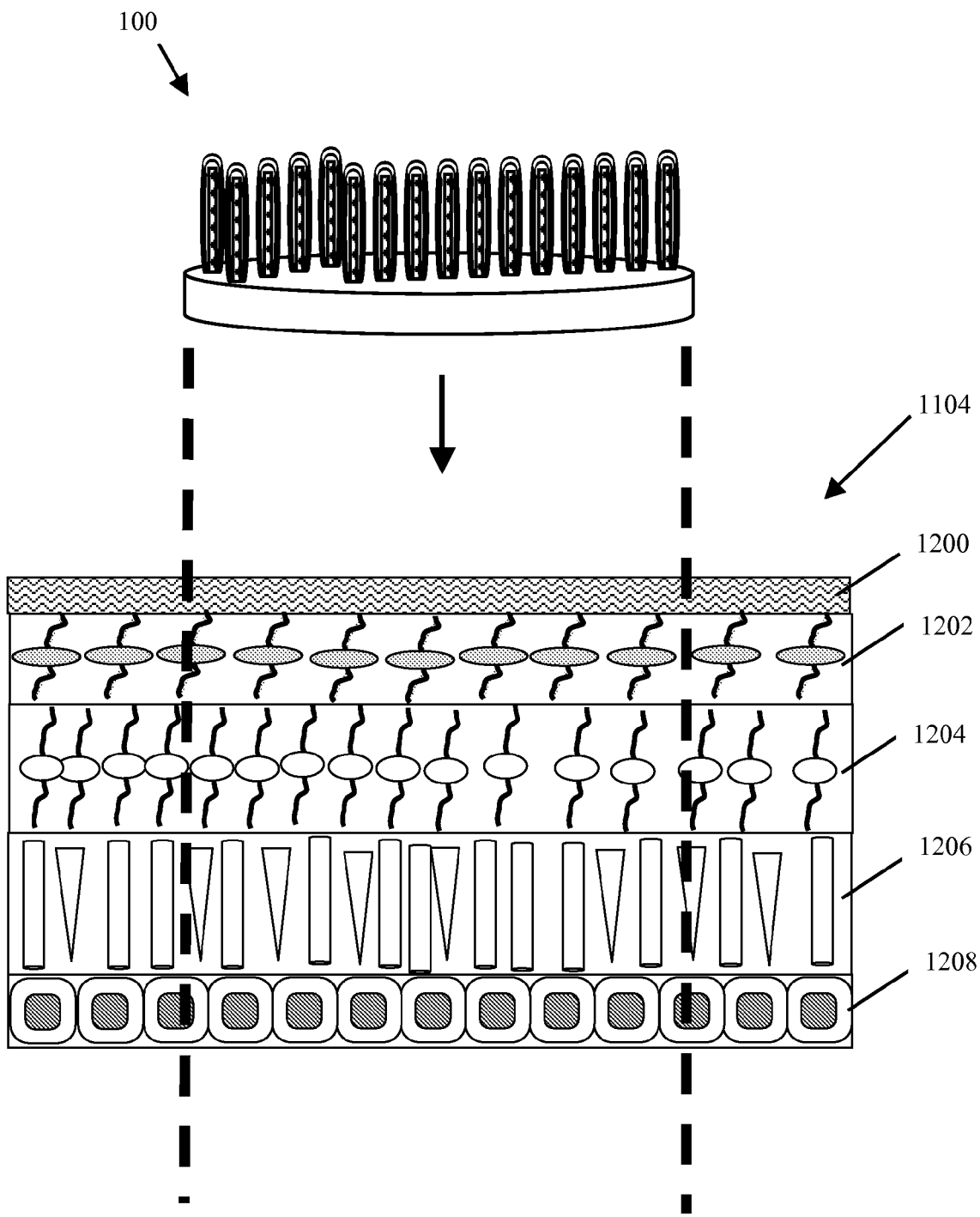
FIG. 12 is a schematic view illustrating the method shown in FIG. 11 in more detail.
Figure 13:
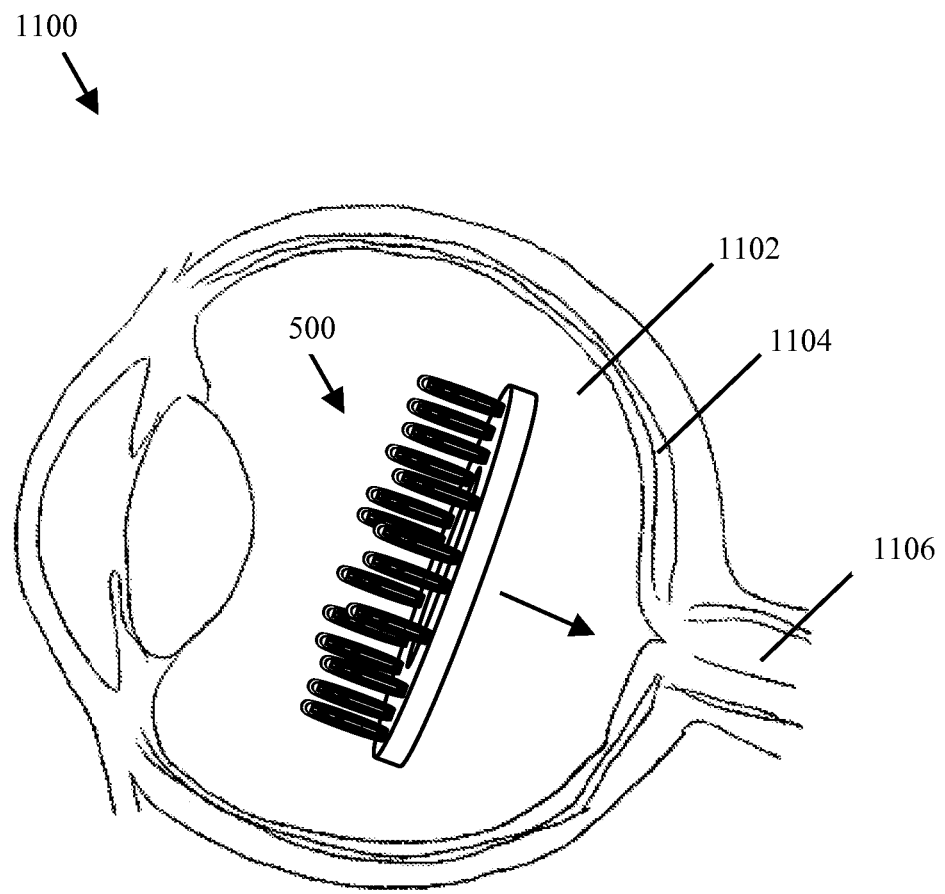
FIG. 13 is a schematic view illustrating another embodiment of a method of implanting a retinal implant in the eye.

FIGS. 11-13 illustrate exemplary methods of implanting retinal implants and/or photoreceptors. Although FIGS. 11-13 and the following description refer to specific retinal implants described above (e.g., retinal implant 100 of FIG. 1A and the retinal implant 500 of FIG. 5) for illustrative purposes, it should be understood that the methods described here can apply to any of the embodiments described herein.

As shown in FIG. 11, the artificial retinal implant 100 can be placed in the vitreous cavity 1102 of the eye 1100, on or in tissue of the retina 1104, or subretinally. In one embodiment, shown in FIG. 11 and in more detail in FIG. 12, the artificial retinal implant 100 can be placed in the foveal region 1108 (as shown in FIG. 11) of the retina. Such a technique can be used when, for example, a patient suffers from macular degeneration. The retinal implant 100 can be implanted in or on top of various layers in the retina 1104, which may be diseased, degenerated, or dead. For example, the retinal implant 100 can be placed on top of the ganglion cells 1202, on top of the bipolar cells 1204, on top of photoreceptor cells 1206, on top of the pigment epithelium 1208, on any other tissue layer in the retina. In another embodiment, retinal tissue (e.g., neuronal cells such as ganglion cells 1202, bipolar cells 1204, and/or photoreceptor cells 1206) can be surgically removed and the retinal implant 100 can be placed within the region of removed tissue. In some embodiments, a biological adhesive can be used to anchor the implant to or within the retina 1104; however, an implant can also be placed on or in the retinal tissue without anchoring such that it is physically secured by the surrounding tissue.

The method for implanting an artificial retinal implant may vary according to the shape and size of the implant, but suitable methods are known in the art. For example, an implantation site can be accessed via retinal dissection techniques, and a retinal implant injector, which can use a fluid to push an implant through a cannula to an appropriate position into the vitreous cavity or subretinal space of the eye, can be used to place the implant. Such techniques are described in more detail in U.S. Patent Publication No. 2002/0099420, titled "Multi-phasic microphotodetector retinal implant with variable voltage and current capability and apparatus for insertion," and U.S. Pat. No. 5,556,423, titled "Independent photoelectric artificial retina device and method of using same," each of which are hereby incorporated by reference in their entirety. Other suitable methods, including standard lensectomy, vitrectomy and retinotomy techniques (e.g., with an irrigation cannula, light pipe, and aspiration vitreous cutter used to create retinal blebs using hydrostatic dissection and enlarging such incisions with vitreoretinal scissors) are described in Chow et al., "The Artificial Silicon Retina Microchip for the Treatment of Vision Loss From Retinitis Pigmentosa," Arch Opthalmol. 2004; 122: 460-469, and in U.S. Pat. No. 7,003,354, titled "Artificial Retina Device With Stimulating And Ground Return Electrodes Disposed On Opposite Side Of The Neuroretina And Method Of Attachment," each of which are hereby incorporated by reference in their entirety.

In some cases, implants can be aligned using a magnetic field following implantation (e.g., in embodiments in which the implant substrate incorporates a magnetic material). However, in other embodiments, photoreceptors can self assemble and attach into a fixed position between a single bipolar cell and the pigment epithelium or other location without the need for external manipulation. Such self-assembly can be achieved by attaching suitably functionalized bridging structures to the top and base of the photoreceptor prior to implantation. For example, a conductive polymer or a carbon nanotube with a chemical group suitable for attachment to the photoreceptor at one end and retina tissue at the other end can be used.

FIG. 13 illustrates another embodiment of a method for implanting an annular artificial retinal implant 500 in the eye. As shown, the annular artificial retinal implant 500 can be placed so as to cover a ring-shaped peripheral area of the retina 1104, which can be advantageous when a patient suffers from retinitis pigmentosa, for example. The artificial retinal implant 500 can be implanted on top of a ring of retinal tissue (e.g., neuronal cells such as ganglion cells, bipolar cells, and/or photoreceptor cells, the pigment epithelium, on any other tissue layer in the retina 1104) or in some cases subretinally, and in other embodiments, a ring of cells in the retina 1104 can be surgically removed and the artificial retinal implant 500 can be placed within the region of the removed cells.

The foregoing retinal implants can be fabricated using a variety of techniques, in many cases those used for semiconductor wafer and nanostructure fabrication. For example, the fabrication of carbon nanostructures to serve as cores, including single and multi-wall carbon nanotubes, is known in the art. By way of example, carbon nanotubes can be fabricated using a variety of techniques, including chemical vapor deposition, laser-ablation, and arc discharge. Methods of fabricating carbon nanotubes are disclosed in more detail in U.S. Pat. Nos. 7,125,534 (Smalley et al., "Catalytic growth of single- and double-wall carbon nanotubes from metal particles"), 7,150,864 (Smalley et al., "Ropes comprised of single-walled and double-walled carbon nanotubes") and 7,354,563, (Smalley et al., "Method for purification of as-produced fullerene nanotubes"), which are hereby incorporated by reference in their entirety. Further, carbon nanostructures can be obtained from commercial suppliers, such as Nanocyl of Sambreville, Belgium (US office in Rockland, Mass., USA), Bayer Materials Science AG of Leverkusen, Germany, and Showa Denko K.K. of Japan.

Further, the fabrication of aligned carbon nanotubes (for example, an upstanding carpet of nanotubes) is known in the art using a variety of techniques. For example, aligned nanotubes can be grown by chemical vapor deposition (CVD), such as plasma-enhanced hot filament chemical vapor deposition using acetylene as a carbon source and ammonia as a dilution and catalytic agent, as described in Huang et al., "Growth of highly oriented carbon nanotubes by plasma-enhanced hot filament chemical vapor deposition," Applied Physics Letters, Vol. 73 No. 26, 3845 (1998), and Ren et al., "Synthesis of Large Arrays of Well-Aligned Carbon Nanotubes on Glass," Science 282, 1105 (1998), each of which is hereby incorporated by reference. Aligned nanotubes have been grown using CVD techniques on patterned silicon substrates using Fe/Mo nanoparticles as catalysts and CO and $H_2$ as feed gases. Such techniques are described in Huang et al., "Growth Mechanism of Oriented Long Single Walled Carbon Nanotubes Using 'Fast-Heating' Chemical Vapor Deposition Process," Nano Letters, Vol. 4, No. 6, 1025-1028 (2004), which is hereby incorporated by reference. Other alignment techniques include the use of magnetic fields, mechanical shear, and gel extrusion, as discussed in Fischer et al., "Magnetically aligned single wall carbon nanotubes films: Preferred orientation and anisotropic properties," Journal of Applied Physics, Vol. 93 No. 4, 2157 (2003), which is hereby incorporated by reference. Inkjet printing can be used in some circumstances. Further, arrays of carbon nanotubes can be commercially obtained from suppliers, as previously mentioned. More details on the formation and alignment of carbon nanotubes can be obtained with reference to U.S. Patent Publication Nos. 2005/0260120 (Smalley et al., "Method For Forming An Array Of Single-Wall Carbon Nanotubes In An Electric Field And Compositions Thereof") and 2005/0249656 (Smalley et al, "Method For Forming A Patterned Array Of Single-Wall Carbon Nanotubes"), all of which are hereby incorporated by reference in their entireties.

In one embodiment of a method for fabricating an artificial retinal implant, cores formed of carbon nanotubes can be deposited onto a substrate. In some cases, the substrate can be roughened or textured, which can be accomplished, for example, via mechanical abrasion or chemical etching. The carbon nanotubes can be deposited via any of a variety of suitable techniques, such as a Langmuir-Blodgett process, spin coating, inkjet printing, or spraying. In other embodiments, as mentioned above, carbon nanotubes can be grown on a substrate using a CVD process.

With reference to the elements in FIG. 1A merely for illustrative purposes, a light-responsive layer 108 can be created by growing first and second layers 110, 112 of semiconductor material, such as Si, on the cores 104 using a chemical bath deposition (CBD) technique. Typically, a CBD reaction involves preparing aqueous or non-aqueous solutions containing appropriate precursor compounds (for example, silicon precursor to create a Si layer, or cadmium precursor solution and selenium precursor solution to create a CdSe layer) and appropriate ligands. Aliquots of these solutions can be combined in a CBD container, and the object (e.g., carbon nanostructure, wafer, or otherwise) onto which the film will be deposited can be immersed in the resulting chemical bath. The object remains immersed for the time required to form a film of the desired thickness. After removal, the objects are rinsed to remove excess reactants and dried for use. It should be understood that the foregoing is a general description and by way of illustration only. CBD processes are described in more detail in U.S. Pat. No. 7,253,014 (Barron et al., "Fabrication Of Light Emitting Film Coated Fullerenes And Their Application For In-Vivo Light Emission"), in U.S. Patent Publication No. 2005/0089684 (Barron et al., "Coated Fullerenes, Composites And Dielectrics Made Therefrom"), and in U.S. Patent Application Publication No. 2006/0145194 (Barron et al., "Method For Creating a Functional Interface Between A Nanoparticle Nanotube or Nanowire, And A Biological Molecule Or System"), each of which is hereby incorporated by reference in its entirety.

The thickness of the light-responsive layer can be adjusted by varying the concentration of precursors and immersion times. For example, increased concentration and/or immersion times can be used to build a thicker coating and can be used to fill in the interstices between the cores or between carbon nanotubes which can make up the bundles that can form the cores. The layer can be built up to form a uniform surface, as previously mentioned. It should be understood that the layer can be deposited either before or after the cores are deposited on the substrate, if a substrate is used.

The CBD process can provide a crystalline semiconductor coating on the core. For example, the crystalline coating can be a single crystal and/or have crystalline regions formed therein. In some cases, the use of carbon nanotube cores can promote the growth of crystalline regions, for example by nucleating growth of the semiconductor material on the carbon nanotube surfaces. Crystalline regions can have advantageous electrical properties, e.g., they can promote high-efficiency current generation and collection in the light-responsive layer. In some embodiments, the deposited material in the light-responsive layer can be annealed to facilitate the production of a coating of crystalline material. By way of example, such annealing can be performed at an elevated temperature (e.g., in a range of about 300-1000 degrees Celsius) and for a suitable duration (e.g., a few second to a few hours).

Insulating layers also can be deposited using CBD or other known techniques. In some cases, a light-responsive layer may need to be removed, e.g., by chemically etching a portion of the layer off the core, as is known in the art. Etching may involve masking or capping techniques to target the area etched, and/or controlled immersion into etchant baths (e.g., inverting the implant and inserting a portion into the bath).

The foregoing is by way of example only, and a range of variations are possible and are intended to be within the scope of this disclosure. For example, in other embodiments, other processes for fabricating the retinal implant can be used, including without limitation chemical vapor deposition, molecular beam epitaxy, atomic layer deposition, and electrochemical deposition.

EXAMPLE

The following procedures, which are illustrative in nature and provided only as non-limiting examples, describe CBD procedures that have been used for depositing semiconductor materials on carbon nanotubes. These procedures can be used for the creation of light-responsive layers on carbon cores and for forming artificial retinal implants such as those described herein. The procedures described in aforementioned U.S. Pat. No. 7,253,014 (Barron et al., "Fabrication Of Light Emitting Film Coated Fullerenes And Their Application For In-Vivo Light Emission"), and in U.S. Patent Publication No. 2005/0089684 (Barron et al., "Coated Fullerenes, Composites And Dielectrics Made Therefrom"), can also be used.

I. Exemplary Procedure for preparation of Chemical Bath Deposition (CBD) solution for deposition of Cadmium Selenide (CdSe) onto carbon nanotube (CNT) substrates A. Preparation of stock solutions (10 mL total volumes).
1. 0.1 M Cadmium Sulfate solution: dissolve 0.209 g of Cadmium Sulfate ($CdSO_4$) with de-ionized water (d.i. HO) to a final volume of 10 mL.
2. 0.8 M Sodium Citrate solution: dissolve 2.32 g of Sodium Citrate Dihydrate ($Na_3C_6H_5O_7.2H_2O$) with d.i. $H_2O$ to a final volume of 10 mL.
3. 1.5 M Ammonia solution: dilute 1 mL of concentrated Ammonium Hydroxide (NHOH) solution (conc=15 M $NH_3$) with d.i. $H_2O$ to a final volume of 10 mL.
4. 0.01 M Sodium Sulfite: dissolve 0.013 g of Sodium Sulfite ($Na_2SO_3$) with d.i. $H_2O$ to a final volume of 10 mL. NOTE: This solution was prepared immediately before use.
5. 0.1 M DMSU solution (stabilized): dissolve 0.151 g of 1,1-Dimethyl-2-Selenourea ($C_3H_8N_2Se$, DMSU) with 0.01 M Sodium Sulfite solution to a final volume of 10 mL. NOTE: This solution was prepared immediately before use.
6. 0.005 M Mercury (II) Chloride solution: dissolve 0.014 g of Mercury (II) Chloride ($HgCl_2$) with d.i. $H_2O$ to a final volume of 10 mL.

B. Preparation of CBD solution (10 mL total volume, Final pH=9.6-9.7).
1. Place 1.7 mL of d.i. $H_2O$ in a vial.
2. Add 3.0 mL of the 0.1 M Cadmium Sulfate solution to the vial.
3. Add 1.5 mL of the 0.8 M Sodium Citrate solution to the vial.
4. Add 1.2 mL of the 1.5 M Ammonia solution to the vial.
5. Add 2.6 mL of the 0.1 M DMSU solution (stabilized) to the vial.

C. Preparation of the substrate.
1. CNT substrates can be immersed into enough d.i. $H_2O$ to completely cover their surfaces at a rate that is slow enough to gently displace any trapped air with water.
2. The substrates are left soaking in water for 10 min or until they are needed for Step D1.
3. Upon removing the substrates from the water, excess water is allowed to drip from the surface; however, they are not allowed to dry, but are instead dipped into the CBD solution wet (Step D1).

D. Coating of the substrate.
1. Immediately after completing Step C3, immerse substrate into the resultant CBD solution within the vial. Leave at room temperature for 12 h. Note: Substrate was oriented vertically or with the side of interest tilted face down to minimize the unwanted deposition of bulk precipitate due to gravity.
2. After 12 h. have passed, remove the substrate from the CBD solution and rinse it with copious amounts (~50 mL) of d.i. $H_2O$ to remove any reagents and adsorbed precipitate.

3. Samples are allowed to dry in air at room temperature before characterization.

E. Doping of the coated substrates.
1. Doping of coated-CNT substrates with Hg to enhance the n-type conductivity of the CdSe coating may be accomplished by immersing the substrates after Step D2 into a 0.005 M $HgCl_2$ solution for 15 min at room temperature.
2. After 15 minutes have passed, remove the substrate from the solution and rinse it with copious amounts (~50 mL) of d.i. $H_2O$ to remove any reagents.
3. Samples are allowed to dry in air at room temperature before characterization.

F. Thermal annealing of the coated substrates.
1. Thermal annealing of either doped coated-CNT substrates from Step E3 or undoped coated-CNT substrates from Step D3, for improving the photoconductivity of the CdSe coatings, can be affected by placement in an oven at 300° C. under a normal atmosphere of air for 1 h.
2. After 1 h. has passed, the samples are removed from the oven and allowed to cool to room temperature before further modification or characterization.

II. Exemplary procedure for preparation of Chemical Bath Deposition (CBD) solution for deposition of in-situ Cu-doped Cadmium Sulfide (CdS) onto CdSe-coated carbon nanotube (CNT) substrates.

A. Preparation of stock solutions (10 mL total volumes).
1. 1.0 M Cadmium Sulfate solution: dissolve 2.09 g of Cadmium Sulfate ($CdSO_4$) with de-ionized water (d.i. $H_2O$) to a final volume of 10 mL.
2. 15 M Ammonia solution: use concentrated Ammonium Hydroxide ($NH_4OH$) solution (conc=15 M $NH_3$) as purchased.
3. 1.0 M Thiourea solution: dissolve 0.761 g of Thiourea ($CH_4N_2S$, TU) with de-ionized water (d.i. H2O) to a final volume of 10 mL.
4. 3.75 M Triethanolamine solution: dissolve 5.59 g Triethanolamine ($C_6H_{15}NO_3$, TEA) with d.i. $H_2O$ to a final volume of 10 mL.
5. 0.1 M Cupric Chloride solution: dissolve 0.170 g of Cupric Chloride Dihydrate ($CuCl_2.2H_2O$) with de-ionized water (d.i. $H_2O$) to a final volume of 10 mL.

B. Preparation of CBD solution (10 mL total volume).
1. Place 7.91 mL of d.i. $H_2O$ in a vial.
2. Add 0.500 mL of the 1.0 M Cadmium Sulfate solution to the vial.
3. Add 0.467 mL of the 3.75 M Triethanolamine solution to the vial.
4. Add 0.500 mL of the 15 M Ammonia solution to the vial.
5. Add 0.120 mL of the 0.1 M Cupric Chloride solution to the vial.
6. Add 0.500 mL of the 1.0 M Thiourea solution to the vial.

C. Preparation of the substrate.
1. Coated-CNT substrates are immersed into enough d.i. $H_2O$ to completely cover their surfaces at a rate that is slow enough to gently displace any trapped air with water.
2. The substrates are left soaking in water for a minimum of 10 min or until they are needed for Step D1.
3. Upon removing the substrates from the water, excess water is allowed to drip from the surface; however, they are not allowed to dry, but are instead dipped into the CBD solution wet (Step D1).

D. Coating of the substrate.
1. Immediately after completing Step C3, immerse substrate into the resultant CBD solution within the vial. Note: Substrate was oriented vertically or with the side of interest tilted face down to minimize the unwanted deposition of bulk precipitate due to gravity.
2. Place vial in a heating bath @ 80° C. for 2 h.
3. After 2 h. have passed, remove the substrate from the CBD solution and rinse it with copious amounts (~50 mL) of d.i. $H_2O$ to remove any reagents and adsorbed precipitate.
4. Samples are allowed to dry in air at room temperature before characterization.

III. Exemplary procedure for preparation of Chemical Bath Deposition (CBD) solution for deposition of un-doped Cadmium Sulfide (CdS) onto CdSe-coated carbon nanotube (CNT) substrates and ex situ Cu doping.

A. Preparation of stock solutions (10 mL total volumes).
1. 1.0 M Cadmium Sulfate solution: dissolve 2.09 g of Cadmium Sulfate ($CdSO_4$) with de-ionized water (d.i. $H_2O$) to a final volume of 10 mL.
2. 15 M Ammonia solution: use concentrated Ammonium Hydroxide ($NH_4OH$) solution (conc=15 M $NH_3$) as purchased.
3. 1.0 M Thiourea solution: dissolve 0.761 g of Thiourea ($CH_4N_2S$, TU) with de-ionized water (d.i. $H_2O$) to a final volume of 10 mL.
4. 3.75 M Triethanolamine solution: dissolve 5.59 g Triethanolamine ($C_6H_{15}NO_3$, TEA) with d.i. $H_2O$ to a final volume of 10 mL.
5. 0.1 M Cupric Chloride solution: dissolve 0.170 g of Cupric Chloride Dihydrate ($CuCl_2.2H_2O$) with de-ionized water (d.i. $H_2O$) to a final volume of 10 mL.
6. 0.005 M Cupric Chloride solution: dilute 0.5 mL of 0.1 M Cupric Chloride solution with de-ionized water (d.i. $H_2O$) to a final volume of 10 mL.

B. Preparation of CBD solution (10 mL total volume).
1. Place 8.03 mL of d.i. $H_2O$ in a vial.
2. Add 0.500 mL of the 1.0 M Cadmium Sulfate solution to the vial.
3. Add 0.467 mL of the 3.75 M Triethanolamine solution to the vial.
4. Add 0.500 mL of the 15 M Ammonia solution to the vial.
5. Add 0.500 mL of the 1.0 M Thiourea solution to the vial.

C. Preparation of the substrate.
1. Coated-CNT substrates are immersed into enough d.i. $H_2O$ to completely cover their surfaces at a rate that is slow enough to gently displace any trapped air with water.
2. The substrates are left soaking in water for a minimum of 10 min or until they are needed for Step D1.
3. Upon removing the substrates from the water, excess water is allowed to drip from the surface; however, they are not allowed to dry, but are instead dipped into the CBD solution wet (Step D1).

D. Coating of the substrate.
1. Immediately after completing Step C3, substrates are immersed into the resultant CBD solution within the vial. Note: Substrates are oriented vertically or with the side of interest tilted face down to minimize the unwanted deposition of bulk precipitate due to gravity.
2. Place vial in a heating bath @80° C. for 2 h.
3. After 2 h. have passed, remove the substrate from the CBD solution and rinse it with copious amounts (~50 mL) of d.i. $H_2O$ to remove any reagents and adsorbed precipitate.
4. Samples are allowed to dry in air at room temperature before characterization.

E. Ex situ doping of the coating.
1. Immerse CdS-coated substrate from Step D4 into the 0.005 M Cupric Chloride solution for 30 s. The film color will change from bright orange to dark brown as Cu doping occurs.
2. After 30 s have passed, remove sample from solution and rinse it with copious amounts (~50 mL) of d.i. $H_2O$ to remove any reagents.

IV. Exemplary Procedure for preparation of Chemical Bath Deposition (CBD) solution for deposition of in situ Cu-doped Zinc Sulfide (ZnS) onto CdSe-coated carbon nanotube (CNT) substrates.
A. Preparation of stock solutions (10 mL total volumes).
1. 1.0 M Zinc Sulfate solution: dissolve 2.88 g of Zinc Sulfate Heptahydrate ($ZnSO_4.7H_2O$) with de-ionized water (d.i. $H_2O$) to a final volume of 10 mL.
2. 0.8 M Sodium Citrate solution: dissolve 2.32 g of Sodium Citrate Dihydrate ($Na_3C_6H_5O_7.2H_2O$) with d.i. $H_2O$ to a final volume of 10 mL.
3. 15 M Ammonia solution: concentrated Ammonium Hydroxide ($NH_4OH$) solution (conc=15 M $NH_3$) as purchased.
4. 3.75 M Triethanolamine solution: dissolve 5.59 g Triethanolamine ($C_6H_{15}NO_3$, TEA) with d.i. $H_2O$ to a final volume of 10 mL.
5. 0.1 M Cupric Chloride solution: dissolve 0.170 g of Cupric Chloride Dihydrate ($CuCl_2.2H_2O$) with de-ionized water (d.i. $H_2O$) to a final volume of 10 mL.
6. 1.0 M Thiourea solution: dissolve 0.761 g of Thiourea ($CH_4N_2S$, TU) with de-ionized water (d.i. $H_2O$) to a final volume of 10 mL.

B. Preparation of CBD solution (10 mL total volume, Final pH=10.0-10.1).
1. Place 7.16 mL of d.i. $H_2O$ in a vial.
2. Add 0.150 mL of the 1.0 M Zinc Sulfate solution to the vial.
3. Add 0.560 mL of the 0.8 M Sodium Citrate solution to the vial.
4. Add 0.200 mL of the 15 M Ammonia solution to the vial.
5. Add 0.400 mL of the 3.75 M Triethanolamine solution to the vial.
6. Add 0.036 mL of the 0.1 M Cupric Chloride solution to the vial.
7. Add 1.50 mL of the 1.0 M Thiourea solution to the vial.

C. Preparation of the substrate.
1. Coated-CNT substrates are immersed into enough d.i. $H_2O$ to completely cover their surfaces at a rate that is slow enough to gently displace any trapped air with water.
2. The substrates are left soaking in water for a minimum of 10 min or until they are needed for Step D1.
3. Upon removing the substrates from the water, excess water is allowed to drip from the surface; however, they are not allowed to dry, but are instead dipped into the CBD solution wet (Step D1).

D. Coating of the substrate.
1. Immediately after completing Step C3, immerse substrate into the resultant CBD solution within the vial. Note: Substrates are oriented vertically or with the side of interest tilted face down to minimize the unwanted deposition of bulk precipitate due to gravity.
2. Place vial in a heating bath @80° C. for 4 h.
3. After 4 h. have passed, remove the substrate from the CBD solution and rinse it with copious amounts (~50 mL) of d.i. $H_2O$ to remove any reagents and adsorbed precipitate.
4. Samples are allowed to dry in air at room temperature before characterization.

V. Exemplary Procedure for preparation of Chemical Bath Deposition (CBD) solution for deposition of un-doped Zinc Sulfide (ZnS) onto CdSe-coated carbon nanotube (CNT) substrates and ex situ Cu doping.
A. Preparation of stock solutions (10 mL total volumes).
1. 1.0 M Zinc Sulfate solution: dissolve 2.88 g of Zinc Sulfate Heptahydrate ($ZnSO_4.7H_2O$) with de-ionized water (d.i. $H_2O$) to a final volume of 10 mL.
2. 0.8 M Sodium Citrate solution: dissolve 2.32 g of Sodium Citrate Dihydrate ($Na_3C_6H_5O_7.2H_2O$) with d.i. $H_2O$ to a final volume of 10 mL.
3. 15 M Ammonia solution: use concentrated Ammonium Hydroxide ($NH_4OH$) solution (conc=15 M $NH_3$) as purchased.
4. 3.75 M Triethanolamine solution: dissolve 5.59 g Triethanolamine ($C_6H_{15}NO_3$, TEA) with d.i. H2O to a final volume of 10 mL.
5. 0.1 M Cupric Chloride solution: dissolve 0.170 g of Cupric Chloride Dihydrate ($CuCl_2.2H_2O$) with de-ionized water (d.i. $H_2O$) to a final volume of 10 mL.
6. 0.005 M Cupric Chloride solution: dilute 0.5 mL of 0.1 M Cupric Chloride solution with de-ionized water (d.i. $H_2O$) to a final volume of 10 mL.
7. 1.0 M Thiourea solution: dissolve 0.761 g of Thiourea ($CH_4N_2S$, TU) with de-ionized water (d.i. $H_2O$) to a final volume of 10 mL.

B. Preparation of CBD solution (10 mL total volume, Final pH=10.0-10.1).
1. Place 7.20 mL of d.i. $H_2O$ in a vial.
2. Add 0.150 mL of the 1.0 M Zinc Sulfate solution to the vial.
3. Add 0.560 mL of the 0.8 M Sodium Citrate solution to the vial.
. Add 0.200 mL of the 15 M Ammonia solution to the vial.
5. Add 0.400 mL of the 3.75 M Triethanolamine solution to the vial.
6. Add 1.50 mL of the 1.0 M Thiourea solution to the vial.

C. Preparation of the substrate.
1. Coated-CNT substrates are immersed into enough d.i. $H_2O$ to completely cover their surfaces at a rate that is slow enough to gently displace any trapped air with water.
2. The substrates are left soaking in water for a minimum of 10 min or until they are needed for Step D1.
3. Upon removing the substrates from the water, excess water is allowed to drip from the surface; however, they are not allowed to dry, but are instead dipped into the CBD solution wet (Step D1).

D. Coating of the substrate.
1. Immediately after completing Step C3, immerse substrate into the resultant CBD solution within the vial. Note: Substrate should be oriented vertically or with the side of interest tilted face down to minimize the unwanted deposition of bulk precipitate due to gravity.
2. Place vial in a heating bath @80° C. for 4 h.
3. After 4 h. have passed, remove the substrate from the CBD solution and rinse it with copious amounts (~50 mL) of d.i. $H_2O$ to remove any reagents and adsorbed precipitate.
4. Samples are allowed to dry in air at room temperature before characterization.

E. Ex situ doping of the coating.
1. Immerse CdS-coated substrate from Step D4 into the 0.005 M Cupric Chloride solution for 30 s. The film color will change from bright orange to dark brown as Cu doping occurs.
2. After 30 s have passed, remove sample from solution and rinse it with copious amounts (~50 mL) of d.i. $H_2O$ to remove any reagents.

VI. Reagent Specifications

Cadmium Sulfate ($CdSO_4$)
FW: 208.46 g/mol
Purity: 99%
Grade: ACS Reagent
Vendor: Sigma Aldrich
Product No.: 383082-100G
Sodium Citrate Dihydrate
($Na_3C_6H_5O_7 \cdot 2\ H_2O$)
FW: 294.10 g/mol
Purity: Meets USP Spec
Vendor: Sigma Aldrich
Product No.: S1804-1KG
Sodium Sulfite ($Na_2SO_3$)
FW: 126.04 g/mol
Grade: Certified ACS
Vendor: Fisher Scientific
Product No.: S430-500
1,1-Dimethyl-2-Selenourea
($C_3H_8N_2Se$, DMSU),
Note: Stored in Argon
glove box.
FW: 151.07 g/mol
Purity: 97%
Vendor: Sigma Aldrich
Product No.: 278882-1G
Ammonium Hydroxide
($NH_4OH$) solution,
concentrated
FW: 35.05 g/mol
Grade: Certified ACS
Vendor: Fisher Scientific
Product No.: A669-212
Ammonium Chloride ($NH_4Cl$)
FW: 53.49 g/mol
Grade: Certified ACS
Vendor: Fisher Scientific
Product No.: A661-500

Figure 14:
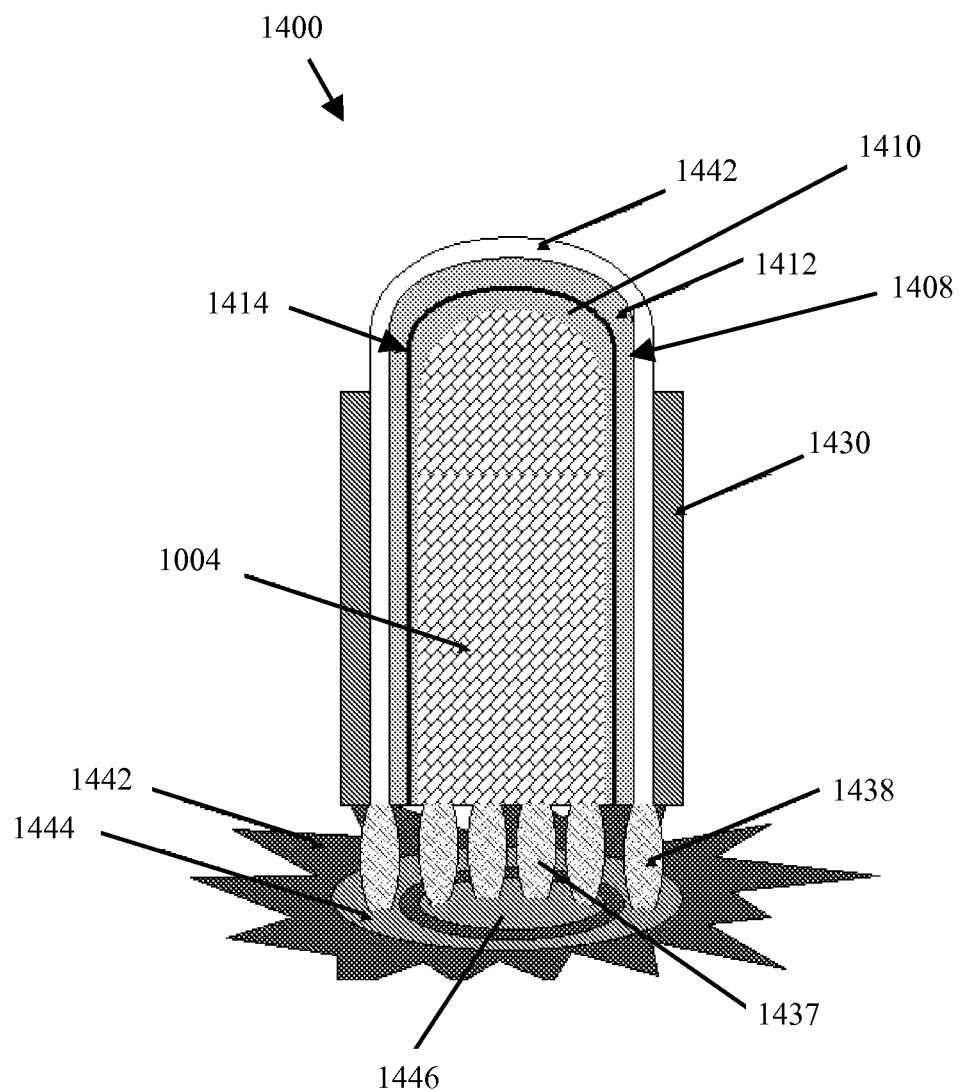
FIG. 14 is a schematic view of one embodiment of an exemplary photosensor for an imaging device which includes a core covered with a light-responsive layer, a dielectric layer, and a wavelength-selective layer.

Thiourea ($CH_4N_2S$, TU)
FW: 76.12 g/mol
Purity: 99.0%
Grade: ACS Reagent
Vendor: Sigma Aldrich
Product No.: T8656-500G
Cupric Chloride Dihydrate ($CuCl_2 \cdot 2\ H_2O$)
FW: 170.48 g/mol
Purity: 99.0%
Grade: ACS Reagent
Vendor: Sigma Aldrich
Product No.: 307483-100G
Zinc Sulfate Heptahydrate
($ZnSO_4 \cdot 7\ H_2O$)
FW: 287.56 g/mol
Purity: 99.0%
Grade: ACS Reagent
Vendor: Sigma Aldrich
Product No.: 221376-500G
Triethanolamine
($C_6H_{15}NO_3$, TEA)
FW: 149.19 g/mol
Purity: 98%
Vendor: Sigma Aldrich
Product No.: T1377-1L
Mercury (II) Chloride ($HgCl_2$)
FW: 271.50 g/mol
Purity: 99.5%
Grade: ACS Reagent
Vendor: Sigma Aldrich
Product No.: 215465-100G The devices and methods disclosed herein are not limited to use in retinal implants. FIG. 14, for example, shows an embodiment of an exemplary sensor 1400 for an imaging device. As shown, the sensor 1400 includes a core 1404 (e.g., carbon nanotube, as previously described) that is coated in part by a light-responsive layer 1408. The light-responsive layer 1408 can include a first layer 1410 and a second layer 1412 (e.g., semiconductor layers, as previously described) which form a junction 1414. A wavelength-selective layer 1442 can cover the light-responsive layer so that the sensor 1400 is responsive to selected wavelengths (e.g., red, green, or blue). A dielectric layer 1430 can be disposed over a portion of the wavelength-selective layer 1442, which can be advantageous in electrically isolating sensors 1400 when a plurality of sensors 1400 are placed adjacent to one another in an array.

The wavelength-selective layer 1442, which can be conductive, can be electrically coupled to a contact 1444 disposed on a back substrate 1442. In other embodiments, the second layer 1412 can be electrically coupled to the contact 1444. Further, the core 1404 can be electrically coupled to another contact 1446 disposed on a back substrate 1442. The back substrate 1442 can include a dielectric surface so as to electrically isolate the contacts 1444, 1446. The coupling mechanism 1437, 1438 to the substrate 1442 can be a metallic connection or pad created via known techniques (e.g., photolithography), and/or can be generated as a consequence of core 1404 fabrication (e.g., in embodiments in which carbon nanotubes are grown directly on the substrate, using CVD for example).

In use, light incident on the sensor 1400 can produce a voltage across the contacts 1444, 1446, as previously described in connection with the retinal implant of FIG. 1A. By sensing the voltage (or alternatively the current, if the contacts 1444, 1446 are connected across an effective resistance) the presence of light incident on the sensor 1400 can be detected. Further, the intensity of the light can be sensed, as it can be proportional to the voltage and/or current developed across the contacts 1444, 1446.

Figure 15:
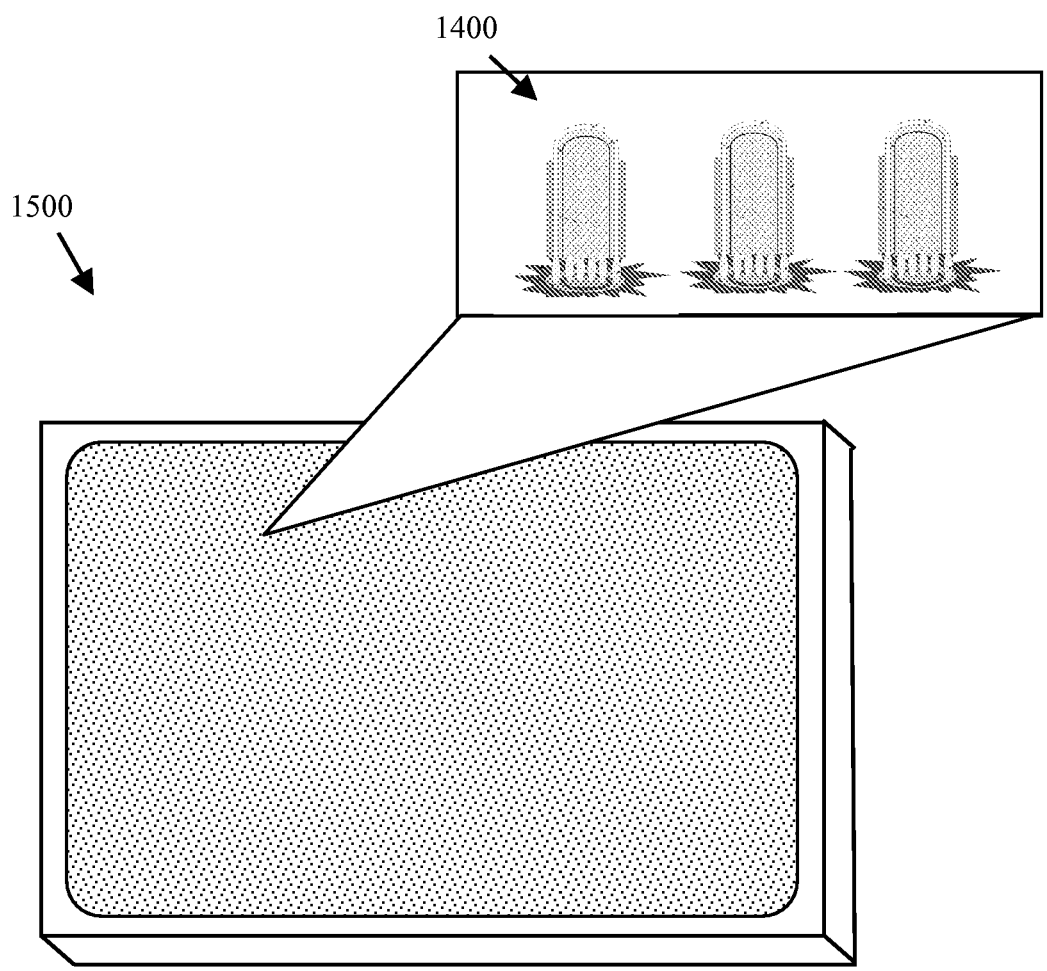
FIG. 15 is a schematic view of one embodiment of an exemplary array of photosensors for an imaging device.

As shown in FIG. 15, a plurality of sensors 1400 can be disposed on the substrate in an array 1500. Sensors 1400 that are responsive to different wavelengths (e.g., because of a wavelength-selective layer) can be interleaved in the array 1500. The signal from each pair of contacts 1444, 1446 can represent or be indicative of a pixel in the image sensed by such an array.

The sensor 1400 can be fabricated using any of the techniques previously described.

One skilled in the art will appreciate further features and advantages based on the above-described embodiments. Accordingly, the claims are not to be limited by what has been particularly shown and described. All publications and references cited herein are expressly incorporated herein by reference in their entirety.

What is claimed is:

1. An implantable photoreceptor, comprising:
   a substrate;
   a core formed from a carbon nanostructure supported by said substrate, wherein the carbon nanostructure comprises a bottom portion of the carbon nanostructure extending from said substrate-and a top portion of the carbon nanostructure above said bottom portion; and
   a light-responsive layer coating said bottom portion of the carbon nanostructure, wherein the top portion of the carbon nanostructure is uncoated by said light responsive layer, and
   wherein the light-responsive layer is effective to generate, in response to light incident thereon, an electric field external to the photoreceptor suitable to induce an action potential in at least one neuron.

2. The implantable photoreceptor of claim 1, wherein the light-responsive layer includes a first layer disposed on the carbon nanostructure and a second layer disposed on the first layer to form a junction therewith, the junction including a depletion region.

3. The implantable photoreceptor of claim 2, wherein at least one of the first and second layer comprises a semiconductor material.

4. The implantable photoreceptor of claim 3, wherein the first layer and second layer comprise semiconductor materials of differing conductivity types.

5. The implantable photoreceptor of claim 3, wherein at least one of the first and second layers comprises at least one of a Group IV semiconductor, a Group III-V semiconductor, a Group II-VI semiconductor, and a Group I-III-VI semiconductor.

6. The implantable photoreceptor of claim 1, wherein the light-responsive layer is effective to generate, in response to light incident thereon, an electric charge in a portion of the photoreceptor, the electric charge producing an electric field external to the photoreceptor suitable to induce an action potential in a neuron.

7. The implantable photoreceptor of claim 1, wherein the electric field has a strength in a range of about 1,000 Volts/cm to about 100,000 Volts/cm.

8. The implantable photoreceptor of claim 1, wherein the electric charge is generated in at least one of the carbon nanostructure and the light-responsive layer.

9. The implantable photoreceptor of claim 1, wherein the light-responsive layer coats at least a portion of the surface of the nanostructure such that a coated end of the nanostructure has a radius of curvature of less than about $10^{-6}$ cm.

10. The implantable photoreceptor of claim 1, wherein the carbon nanostructure has a tapered end to enhance an electric field produced therefrom.

11. The implantable photoreceptor of claim 1, wherein the substrate is disk-shaped.

12. The implantable photoreceptor of claim 1, wherein the substrate is annular.

13. The implantable photoreceptor of claim 1, wherein each carbon nanostructure comprises a carbon nanotube.

14. The implantable photoreceptor of claim 1, further comprising one or more other carbon nanostructures, the carbon nanostructure and the one or more other carbon nanostructures forming a bundle of carbon nanostructures and the light-responsive layer coating at least a portion of the bundle of carbon nanostructures.

15. The implantable photoreceptor of claim 14, wherein the light-responsive layer coats at least a portion of each carbon nanostructure in the bundle of carbon nanostructures.

16. The implantable photoreceptor of claim 14, wherein the bundle has a tapered end so as to enhance an electric field produced therefrom.

17. The implantable photoreceptor of claim 14, wherein the light-responsive layer conformally coats at least one of the carbon nanostructures provided by the bundle of carbon nanostructures.

18. The implantable photoreceptor of claim 1, further comprising an insulating layer disposed on top of the light-responsive layer.

19. The implantable photoreceptor of claim 18, wherein the light-responsive layer is effective to generate, in response to light incident thereon, an electric charge in a portion of the photoreceptor, the electric charge producing an electric field external to the photoreceptor suitable to induce an action potential in at least one neuron adjacent the insulating layer.

20. The implantable photoreceptor of claim 1, wherein the light-responsive layer is operable to generate, an electric charge in a portion of the photoreceptor, the electric charge producing an electric field external to the photoreceptor suitable to induce an action potential in at least one neuron located at least about 50 nm from the implantable photoreceptor.

21. The implantable photoreceptor of claim 1, further comprising an insulating layer disposed on the top portion of the carbon nanostructure.

22. The implantable photoreceptor of claim 1, wherein the carbon nanostructure has a length of about 2 to 50 microns and a width of about 500 to about 2000 nm.

23. The implantable photoreceptor of claim 1, wherein the light-responsive layer has a thickness of about 250 to about 2000 nm.

24. The implantable photoreceptor of claim 1, further comprising a wavelength selective transparent layer disposed over the light-responsive layer.

25. The implantable photoreceptor of claim 1, further comprising one or more semiconductor nanostructure deposited on a surface of the carbon nanostructure core.

* * * * *